(12) United States Patent
Steinmann et al.

(10) Patent No.: US 10,154,913 B2
(45) Date of Patent: Dec. 18, 2018

(54) SURGICAL IMPLANT DEVICES INCORPORATING POROUS SURFACES AND A LOCKING PLATE

(71) Applicant: RENOVIS SURGICAL TECHNOLOGIES, INC., Redlands, CA (US)

(72) Inventors: John C. Steinmann, Redlands, CA (US); Scott Rucker, Austin, TX (US); Tim Rasmussen, Redlands, CA (US); John P. Steinmann, Redlands, CA (US); Trace Cawley, Boca Raton, FL (US); Thomas Ross, Austin, TX (US); Ernesto Rios, Austin, TX (US); Andrew Olcese, Austin, TX (US)

(73) Assignee: Renovis Surgical Technologies, Inc., Redlands, CA (US)

( * ) Notice: Subject to any disclaimer, the term of this patent is extended or adjusted under 35 U.S.C. 154(b) by 53 days.

(21) Appl. No.: 14/504,509

(22) Filed: Oct. 2, 2014

(65) Prior Publication Data

US 2015/0134063 A1 May 14, 2015

Related U.S. Application Data

(63) Continuation-in-part of application No. 13/530,048, filed on Jun. 21, 2012, now abandoned.

(Continued)

(51) Int. Cl.
*A61F 2/44* (2006.01)
*B33Y 80/00* (2015.01)
*A61F 2/30* (2006.01)

(52) U.S. Cl.
CPC ............ *A61F 2/447* (2013.01); *A61F 2/3094* (2013.01); *A61F 2/30771* (2013.01);

(Continued)

(58) Field of Classification Search
CPC . A61F 2/4455–2002/4475; A61F 2310/00023; A61F 2310/00407;

(Continued)

(56) References Cited

U.S. PATENT DOCUMENTS

| 2,721,387 A | * | 10/1955 | Ashuckian | ........... A61C 8/0018 433/173 |
| 5,958,314 A | * | 9/1999 | Draenert | ................... A61F 2/28 264/227 |

(Continued)

FOREIGN PATENT DOCUMENTS

| WO | 2004069106 A1 | 8/2004 | |
| WO | WO 2004069106 A1 | * 8/2004 | ............. A61B 17/86 |

OTHER PUBLICATIONS

Jan. 7, 2015 International Search Report issued in International Patent Application No. PCT/US2014/058759.

(Continued)

*Primary Examiner* — Paul Prebilic
(74) *Attorney, Agent, or Firm* — Clements Bernard Walker PLLC; Christopher L. Bernard

(57) ABSTRACT

A surgical implant device, comprising: a body portion defining a plurality of ports; a plurality of bone screws disposed partially through the plurality of ports defined by the body portion; a locking plate disposed over a head portion of at least one of the plurality of bone screws and engaging a plurality of recesses manufactured into a side of the body portion; and a screw operable for compressing the locking plate against the side of the body portion. Optionally, the surgical implant device further comprising: one or more surfaces comprising a plurality of protruding structures; wherein the body portion and the one or more surfaces comprising the plurality of protruding structures are integrally formed. The one or more surfaces comprising the (Continued)

plurality of protruding structures are formed by an additive manufacturing process.

9 Claims, 34 Drawing Sheets

Related U.S. Application Data

(60) Provisional application No. 61/885,778, filed on Oct. 2, 2013, provisional application No. 61/916,469, filed on Dec. 16, 2013.

(52) U.S. Cl.
CPC ........ *A61F 2/30907* (2013.01); *A61F 2/4465* (2013.01); *B33Y 80/00* (2014.12); *A61F 2002/30011* (2013.01); *A61F 2002/30013* (2013.01); *A61F 2002/3093* (2013.01); *A61F 2002/30509* (2013.01); *A61F 2002/30517* (2013.01); *A61F 2002/30772* (2013.01); *A61F 2002/30774* (2013.01); *A61F 2002/30777* (2013.01); *A61F 2002/30779* (2013.01); *A61F 2002/30784* (2013.01); *A61F 2002/30785* (2013.01); *A61F 2002/30787* (2013.01); *A61F 2002/30841* (2013.01); *A61F 2002/30909* (2013.01); *A61F 2002/30911* (2013.01); *A61F 2002/4475* (2013.01); *A61F 2310/00023* (2013.01); *A61F 2310/00796* (2013.01)

(58) Field of Classification Search
CPC .................. A61F 2/30767–2002/30789; A61F 2002/30838–2002/30848; A61F 2002/30517; A61F 2002/30878; A61F 2002/30891–2002/30896
See application file for complete search history.

(56) References Cited

U.S. PATENT DOCUMENTS

| | | | |
|---|---|---|---|
| 6,139,550 A | 10/2000 | Michelson | |
| 6,419,705 B1* | 7/2002 | Erickson | A61F 2/446 |
| | | | 623/17.11 |
| 6,482,233 B1* | 11/2002 | Aebi | A61F 2/4465 |
| | | | 623/17.11 |
| 7,892,288 B2* | 2/2011 | Blaylock | A61F 2/30771 |
| | | | 623/20.15 |
| 8,496,710 B2 | 7/2013 | Bagga et al. | |
| 9,402,735 B2* | 8/2016 | McDonough | A61B 17/1757 |
| 9,463,097 B2* | 10/2016 | Lechmann | A61B 17/86 |
| 9,486,324 B2* | 11/2016 | Hochschuler | A61F 2/4455 |
| 9,498,218 B2* | 11/2016 | Venu | A61L 27/32 |
| 9,561,117 B2* | 2/2017 | Lechmann | A61F 2/442 |
| 2003/0078668 A1* | 4/2003 | Michelson | A61B 17/7059 |
| | | | 623/17.16 |
| 2007/0166349 A1* | 7/2007 | White | A61L 27/047 |
| | | | 424/423 |
| 2009/0105831 A1* | 4/2009 | Jones | A61B 17/7059 |
| | | | 623/17.16 |
| 2010/0286777 A1* | 11/2010 | Errico | A61F 2/442 |
| | | | 623/17.11 |
| 2010/0298950 A1 | 11/2010 | McDonnell et al. | |
| 2011/0014081 A1* | 1/2011 | Jones | A61F 2/2803 |
| | | | 419/2 |
| 2011/0035010 A1* | 2/2011 | Harrington | A61F 2/4425 |
| | | | 623/17.16 |
| 2012/0277869 A1 | 11/2012 | Siccardi et al. | |
| 2013/0056912 A1 | 3/2013 | O'Neill et al. | |
| 2017/0105847 A1* | 4/2017 | Lee | A61F 2/4611 |

OTHER PUBLICATIONS

May 16, 2017 Supplementary European Search Report for European Patent Application No. EP 14850170.

* cited by examiner

SURGICAL IMPLANT DEVICES INCORPORATING POROUS SURFACES AND A LOCKING PLATE

CROSS-REFERENCE TO RELATED APPLICATIONS

The present patent application/patent claims the benefit of priority: (1) U.S. Provisional Patent Application No. 61/885,778, filed on Oct. 2, 2013, and entitled "POROUS ANTERIOR LUMBAR INTERBODY FUSION CAGE INCLUDING A LOCKING COVER PLATE," and (2) U.S. Provisional Patent Application No. 61/916,469, filed on Dec. 16, 2013, and entitled "IMPLANTABLE MEDICAL DEVICES, INCLUDING POROUS SURFACES WITH FRICTION ENHANCING NEEDLE PROTRUSIONS, LATTICES FORMED FROM IRREGULAR UNIT CELLS, SLIGHTLY IRREGULAR LATTICES, ALL METAL INTERVERTEBRAL DEVICES, FUSION DEVICES HAVING MULTI CIRCULAR CROSS SECTIONAL PROFILES, AND METHODS FOR MAKING SAME USING ADDITIVE MANUFACTURING TECHNIQUES AND TREATING SAME WITH POST PROCESSING STEP TO ENHANCE SURFACE ROUGHNESS," the contents of all of which are incorporated in full by reference herein. The present patent application/patent is also a continuation-in-part (CIP) of U.S. patent application Ser. No. 13/530,048, filed on Jun. 21, 2012, and entitled "IMPLANTABLE MEDICAL DEVICES WITH FRICTION ENHANCING NEEDLE PROTRUSIONS, AND METHODS FOR MAKING SAME USING ADDITIVE MANUFACTURING TECHNIQUES," (now abandoned), the contents of which are incorporated in full by reference herein.

FIELD OF THE INVENTION

The present invention relates generally to novel surgical implant devices incorporating porous surfaces. More specifically, the present invention relates to novel surgical implant devices incorporating porous surfaces for enhancing bony fixation and purchase when implanted. These porous surfaces are formed via novel additive manufacturing techniques and, optionally, novel post-processing manufacturing techniques. They include novel needle-like protrusions and/or lattice structures.

BACKGROUND OF THE INVENTION

When various surgical implant devices, well known to those of ordinary skill in the art, are placed adjacent to or between bony surfaces, it is desirable that adequate friction is present to hold them in place and that surfaces are available for bony fixation and purchase over time. Accordingly, these surgical implant devices often incorporate mechanically-manufactured friction surfaces or utilize friction coatings or bondings for such purposes. However, these mechanically-manufactured friction surfaces, typically consisting of teeth, grooves, striations, or the like, are often not adequate and do little to promote bony purchase. Similarly, these friction coatings or bondings may delaminate and fail.

Thus, what are still needed in the art are improved surgical implant devices that incorporate essentially-integral friction surfaces that are strong and durable, and that provide adequate surface area for bony fixation and purchase, while still being economical to manufacture. Improved additive and post-processing manufacturing techniques now make this possible.

BRIEF SUMMARY OF THE INVENTION

In one exemplary embodiment, a surgical implant device, comprising: a body portion defining a plurality of ports; a plurality of bone screws disposed partially through the plurality of ports defined by the body portion; a locking plate disposed over a head portion of at least one of the plurality of bone screws and engaging a plurality of recesses manufactured into a side of the body portion; and a screw operable for compressing the locking plate against the side of the body portion. Optionally, the surgical implant device further comprising: one or more surfaces comprising a plurality of protruding structures; wherein the body portion and the one or more surfaces comprising the plurality of protruding structures are integrally formed. The one or more surfaces comprising the plurality of protruding structures are formed by an additive manufacturing process. The plurality of protruding structures comprise a plurality of needles. Optionally, the plurality of protruding structures comprise a plurality of needles that are disposed substantially perpendicular to the body portion. Alternatively, the plurality of protruding structures comprise a plurality of needles that are disposed at an angle to the body portion. Preferably, the plurality of protruding structures comprise a plurality of needles that comprise titanium. The body portion defines a hollow interior cavity. Optionally, the body portion defines one or more ports that are configured to receive a bone screw. The body portion defines one or more ports that are configured to allow bony ingrowth. The surgical implant device comprises one of an anterior lumbar interbody fusion cage and a cervical cage.

In another exemplary embodiment, the present invention provides a method for manufacturing a surgical implant device, comprising: providing a body portion; and forming one or more surfaces comprising a plurality of protruding structures on an exterior portion of the body portion; wherein the body portion and the one or more surfaces comprising the plurality of protruding structures are integrally formed. The one or more surfaces comprising the plurality of protruding structures are formed by an additive manufacturing process. The plurality of protruding structures comprise a plurality of needles. Optionally, the plurality of protruding structures comprise a plurality of needles that are disposed substantially perpendicular to the body portion. Alternatively, the plurality of protruding structures comprise a plurality of needles that are disposed at an angle to the body portion. Preferably, the plurality of protruding structures comprise a plurality of needles that comprise titanium. The body portion defines a hollow interior cavity. Optionally, the body portion defines one or more ports that are configured to receive a bone screw. The body portion defines one or more ports that are configured to allow bony ingrowth.

BRIEF DESCRIPTION OF THE DRAWINGS

The present invention is illustrated and described herein with reference to the various drawings, in which like reference numbers are used to denote like device components/method steps, as appropriate, and in which.

FIG. ID conceptually depicts an exemplary surgical implant device surface containing a uniform distribution of outwardly-protruding needles.

FIG. IE conceptually depicts an exemplary surgical implant device surface containing a non-uniform distribution of outwardly-protruding needles.

FIG. IF conceptually depicts an exemplary surgical implant device surface containing a gradient distribution of outwardly-protruding needles.

Figure 1:
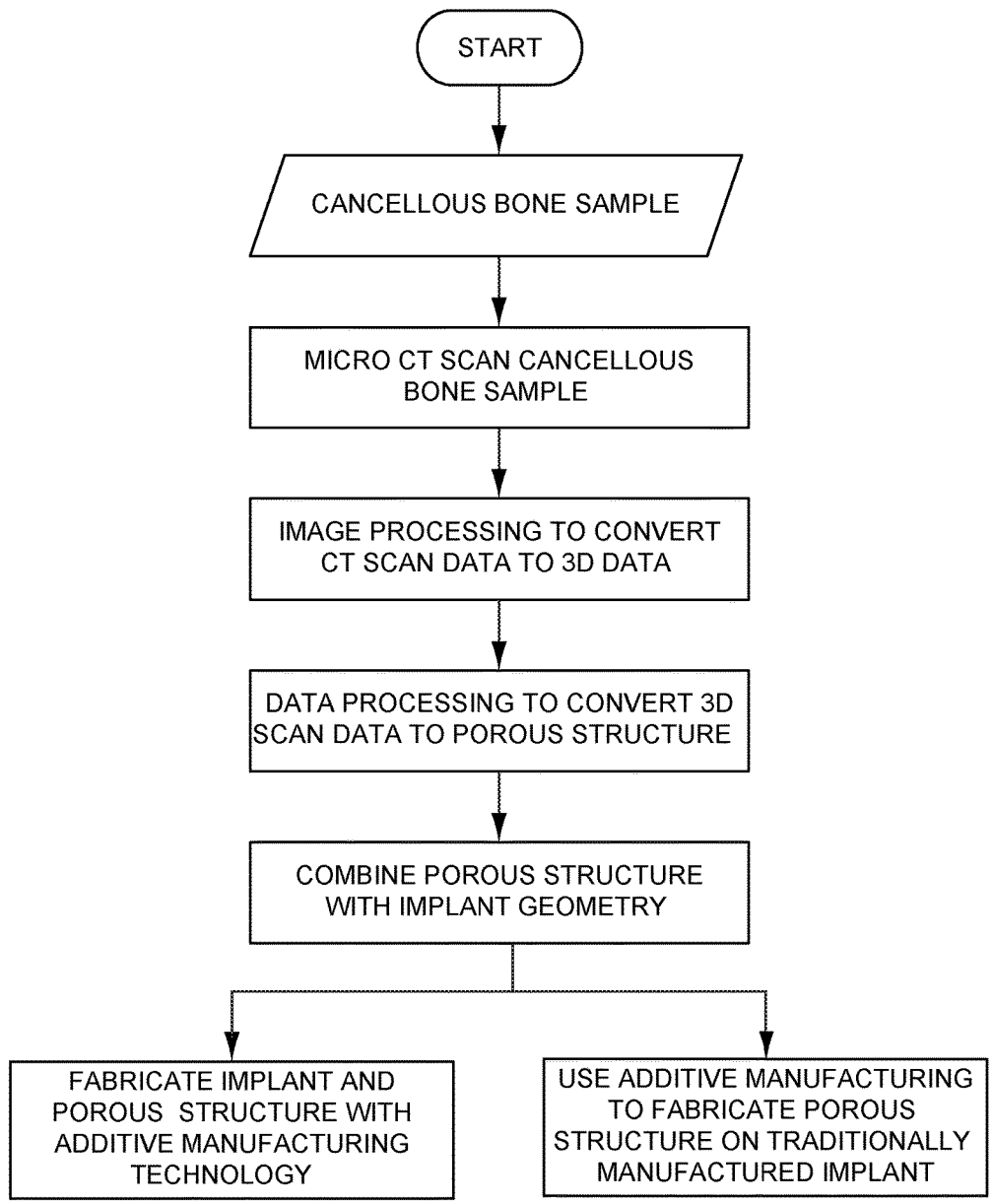
FIG. 1 depicts an exemplary method for producing surgical implant devices having osteo-derived and/or osteo-porous surface(s).
Figure 1A:
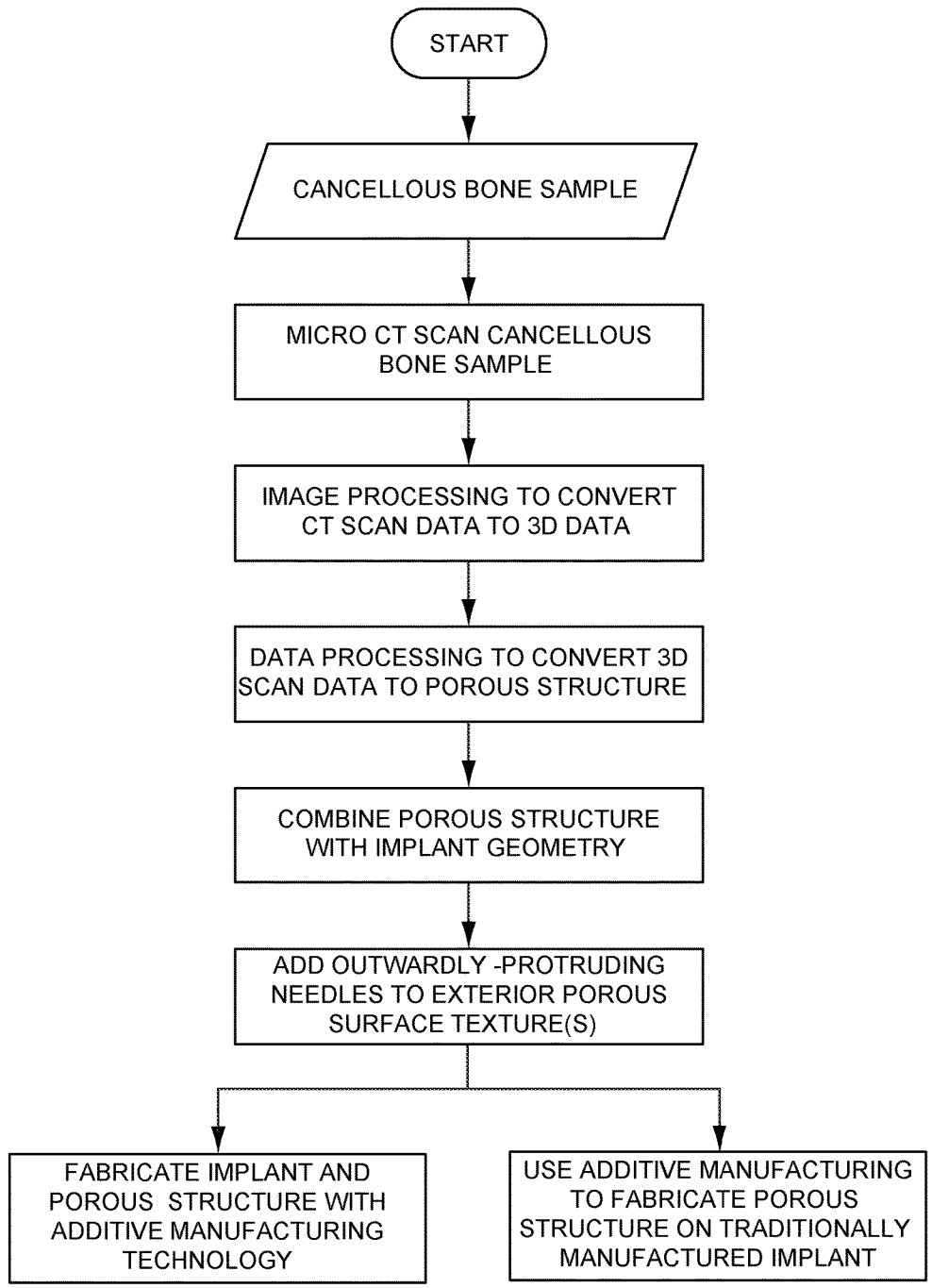
FIG. 1A depicts an exemplary method for producing surgical implant devices having osteo-derived and/or osteo-porous surface(s) with additional outwardly-protruding "needles."
Figure 1B:
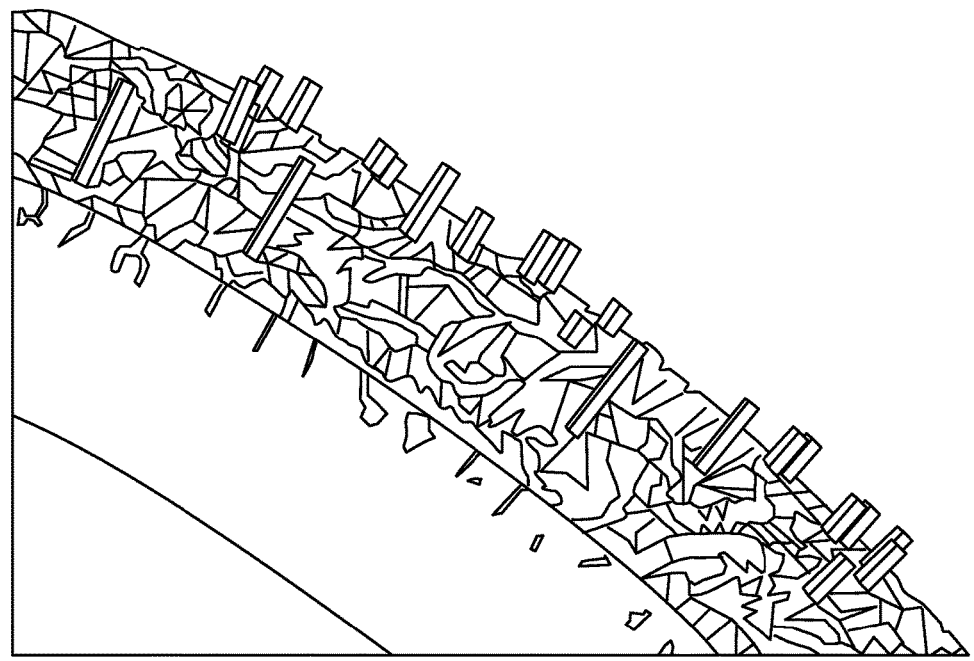
FIG. 1B depicts an exploded section of a computer-generated rendering of an exemplary osteo-derived and/or osteo-porous surface with outwardly-protruding needles.
Figure 1C:
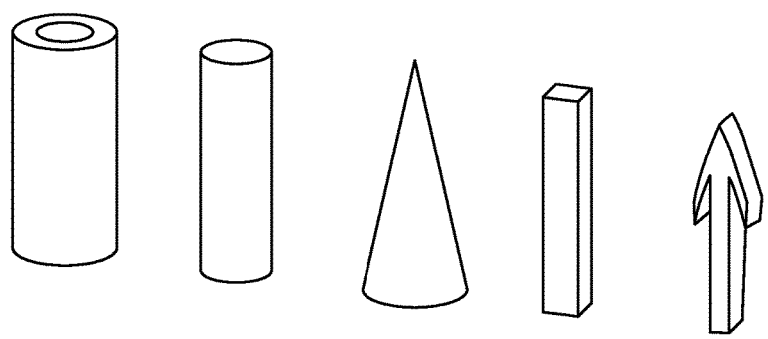
FIG. 1C conceptually depicts various exemplary shapes of outwardly-protruding needles (including, from left to right, tubular, rod-shaped, conical, square/rectangular, and barbed/irregular) useful with the present invention.
Figure 1D:
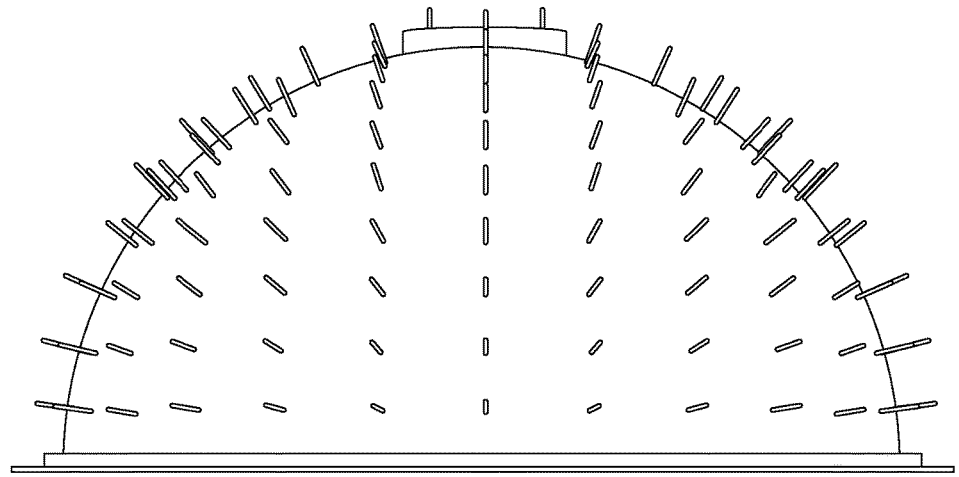
Figure 1E:
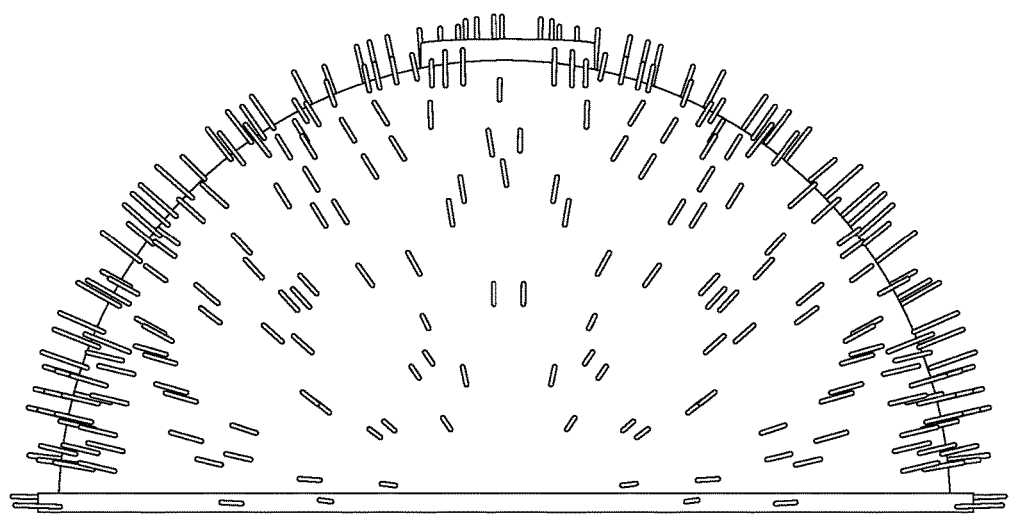
Figure 1F:
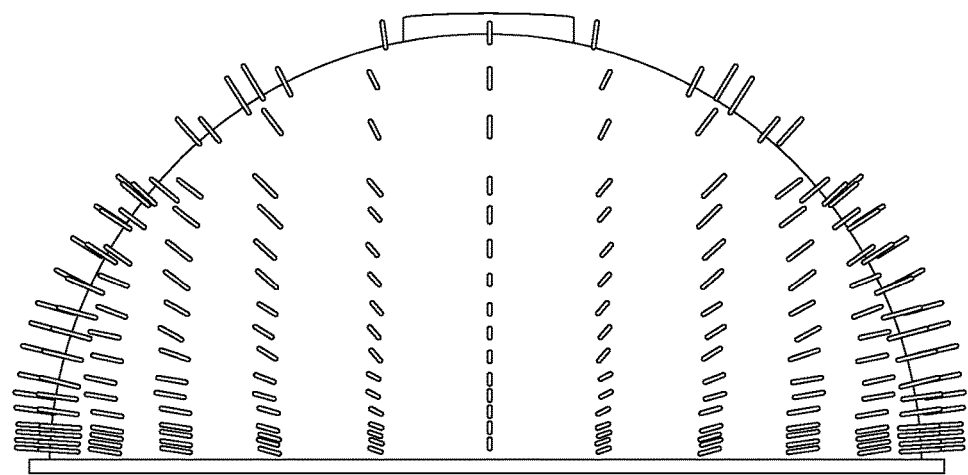
Figure 1G:
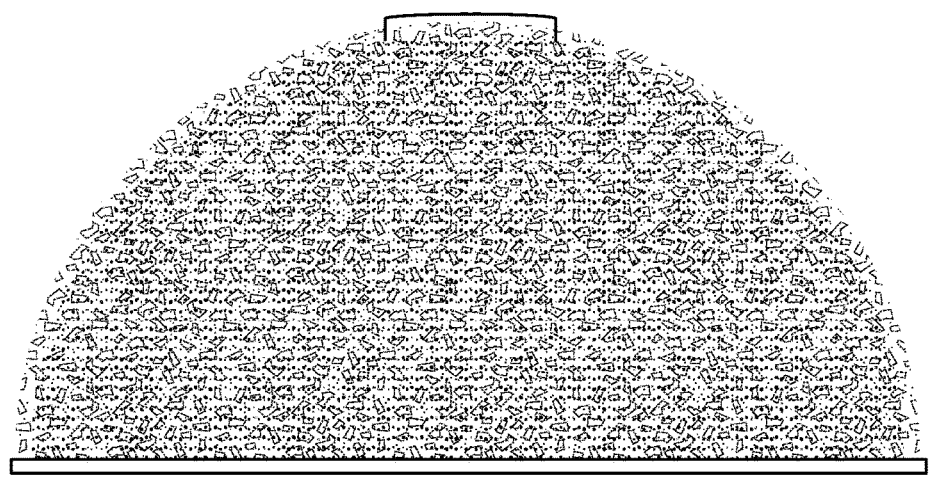

FIG. 1G conceptually depicts an exemplary osteo-porous, osteo-derived, and/or trabecular surgical implant device surface containing a randomized distribution of outwardly-protruding needles.

Figure 1H:
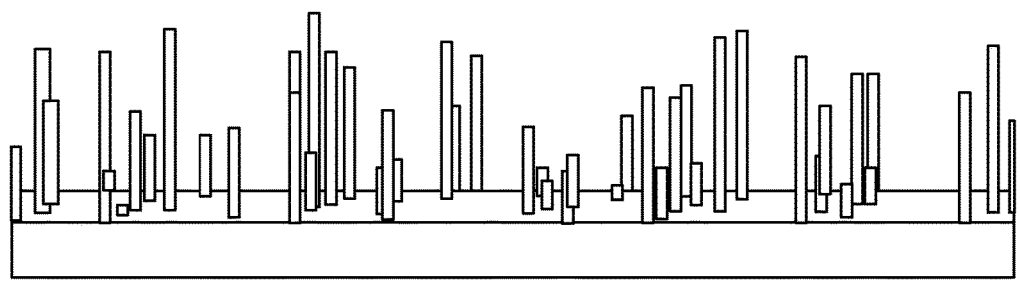

FIG. 1H conceptually depicts an exemplary cross-section of an implant surface containing a randomized distribution of needle heights.

Figure 1I:
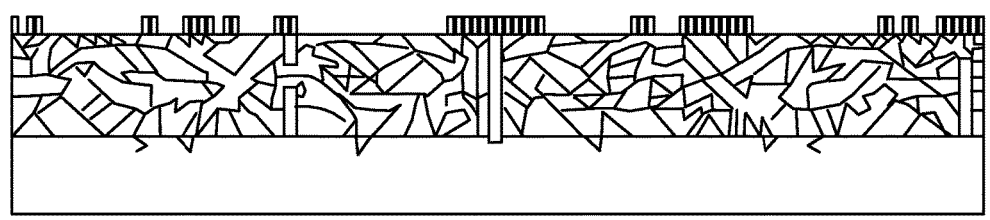

FIG. 1I conceptually depicts an exemplary cross-section of an implant surface containing an exemplary osteo-porous, osteo-derived, and/or trabecular coating with needles anchored to the underlying substrate.

Figure 1J:
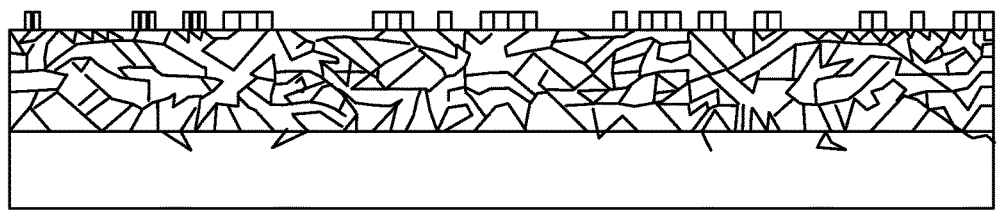
Figure 1K:
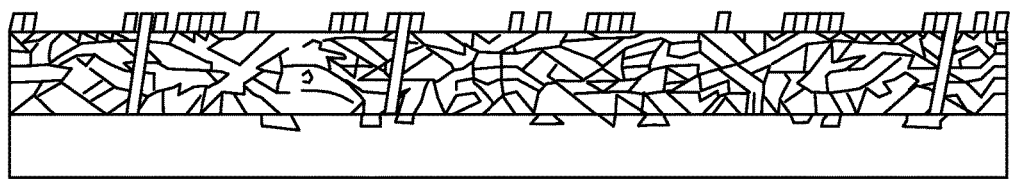

FIG. 1J conceptually depicts an exemplary cross-section of an implant surface containing an exemplary osteo-porous, osteo-derived, and/or trabecular coating with needles anchored to the osteo-porous, osteo-derived, and/or trabecular coating.

FIG. IK conceptually depicts an exemplary cross-section of an implant surface containing an exemplary osteo-porous, osteo-derived, and/or trabecular coating with uniformly tilted needles anchored to the underlying substrate.

Figure 1L:
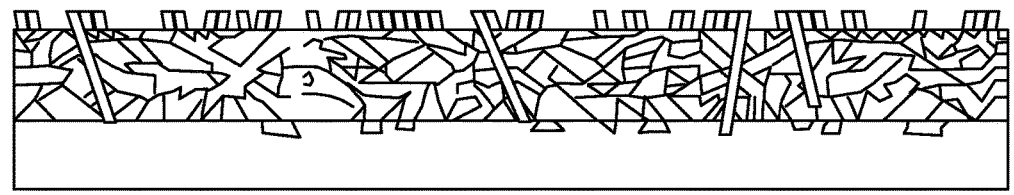

FIG. 1L conceptually depicts an exemplary cross-section of an implant surface containing an exemplary osteo-porous, osteo-derived, and/or trabecular coating with non-uniformly tilted needles anchored to the underlying substrate.

Figure 2:
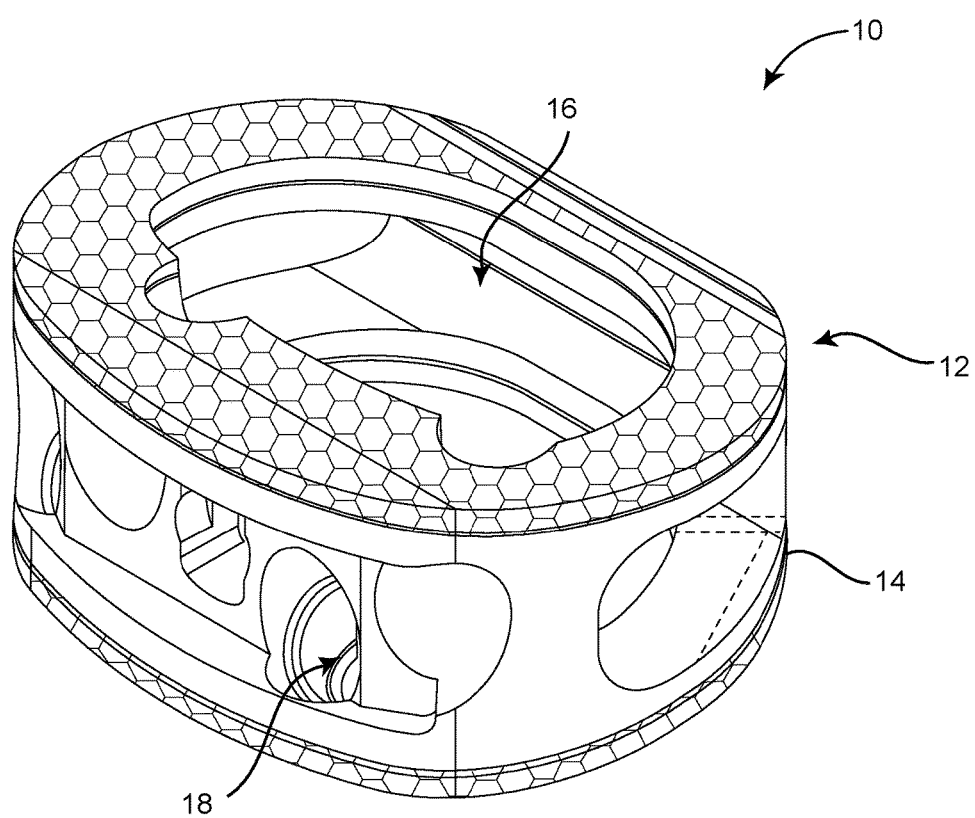

FIG. 2 is a perspective view of one exemplary embodiment of an anterior lumbar interbody fusion (ALIF) cage of the present invention, again highlighting the porous surfaces thereof formed by the techniques of FIG. 1.

Figure 3:
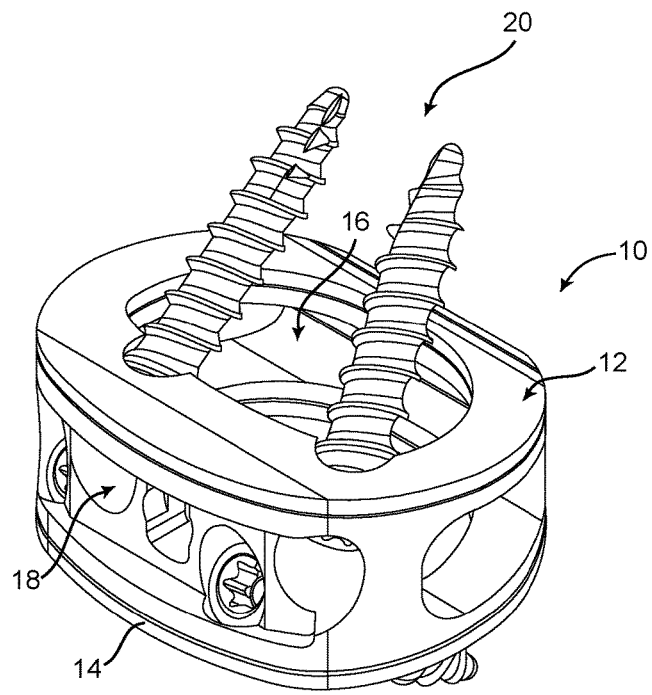
Figure 3A:
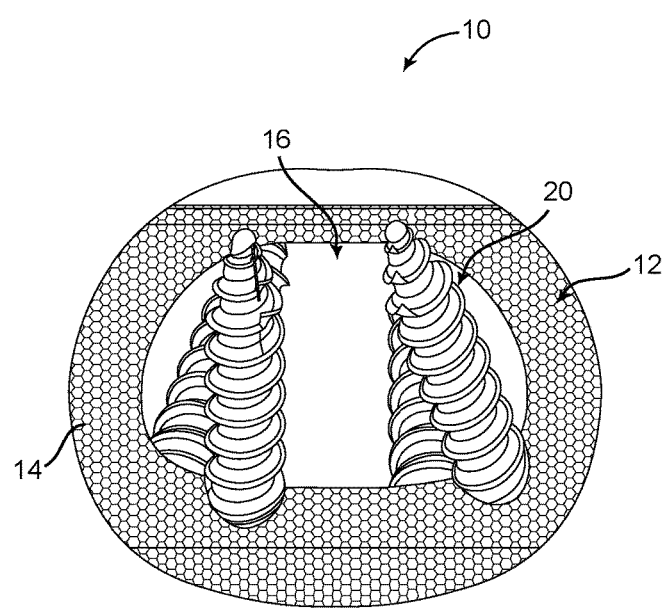
Figure 3B:
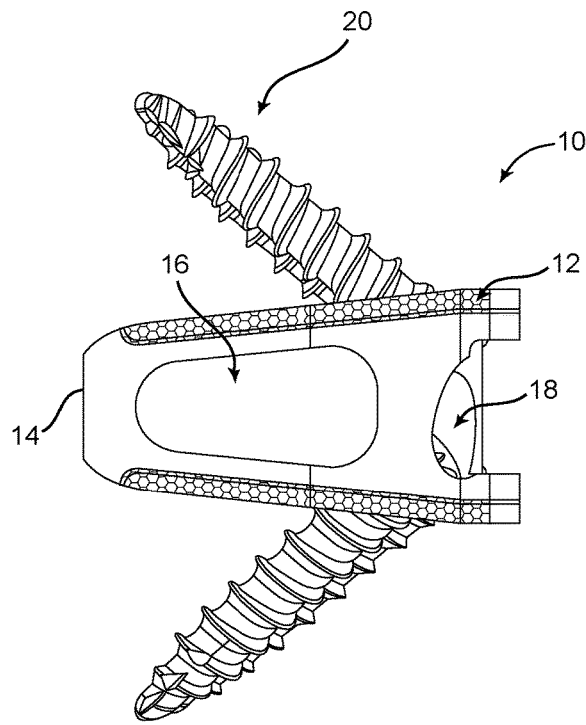
Figure 3C:
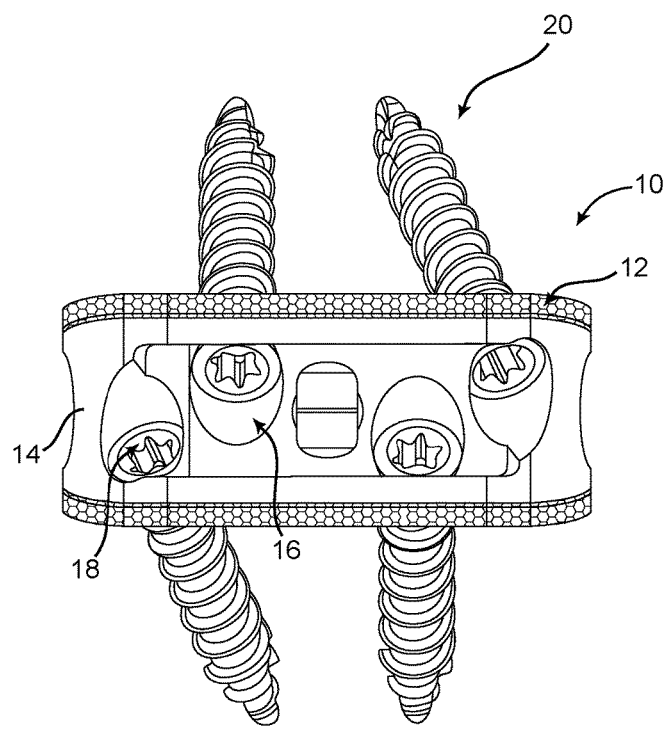

FIG. 3 is a series of perspective and planar views of one exemplary embodiment of the ALIF cage of the present invention, again highlighting the porous surfaces thereof formed by the techniques of FIG. 1.

Figure 4:
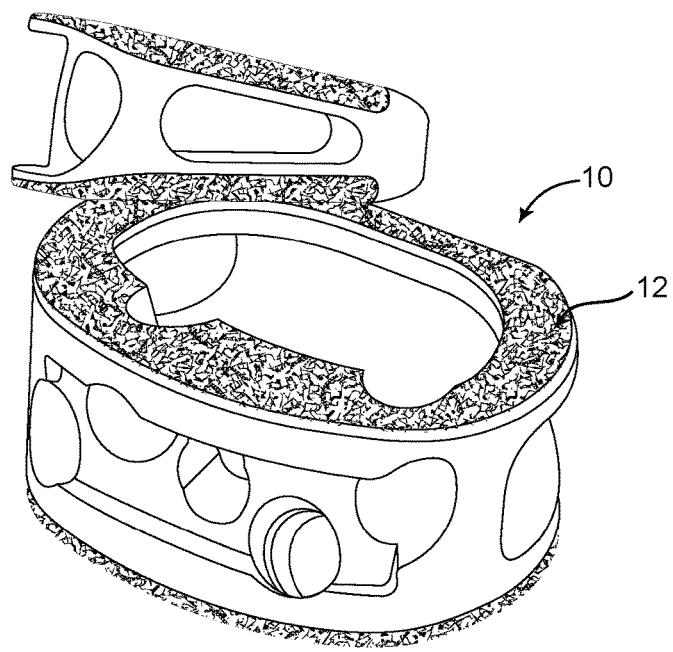

FIG. 4 is a photograph of one exemplary embodiment of the ALIF cage of the present invention, again highlighting the porous surfaces thereof formed by the techniques of FIG. 1.

Figure 5:
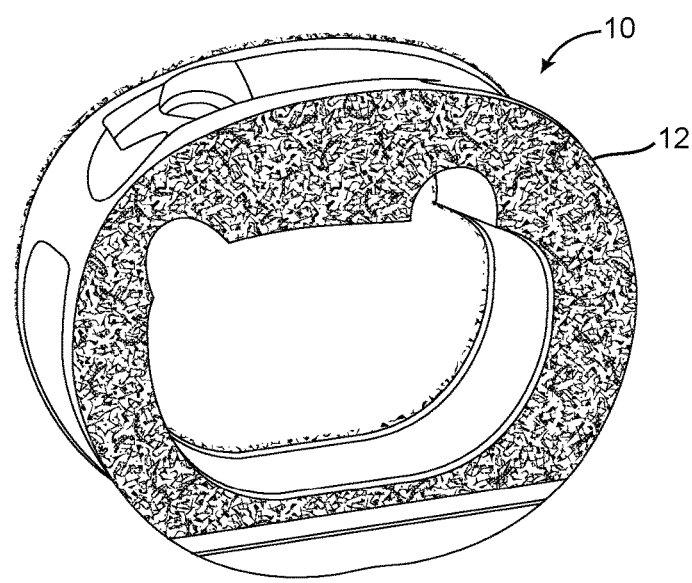

FIG. 5 is another photograph of one exemplary embodiment of the ALIF cage of the present invention, again highlighting the porous surfaces thereof formed by the techniques of FIG. 1.

Figure 6:
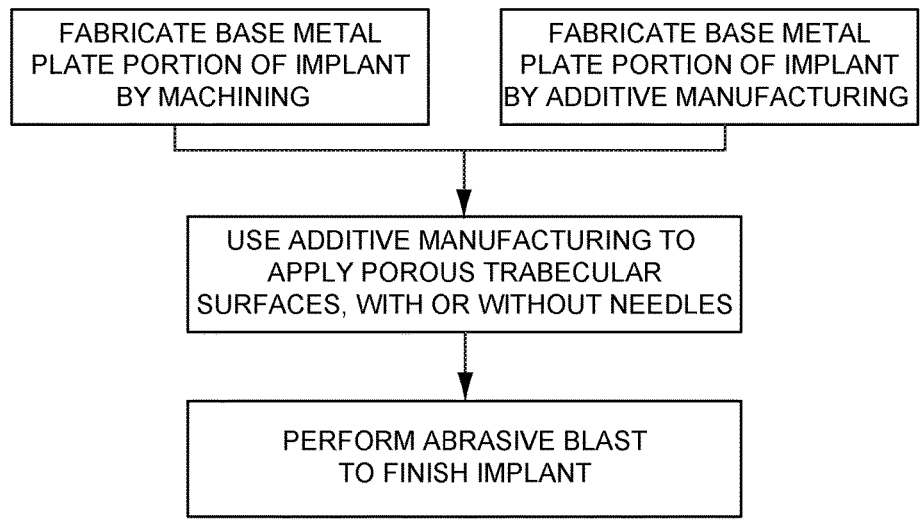

FIG. 6 depicts preferred process flows for manufacturing abrasive-blasted implants in accordance with the invention.

Figure 7:
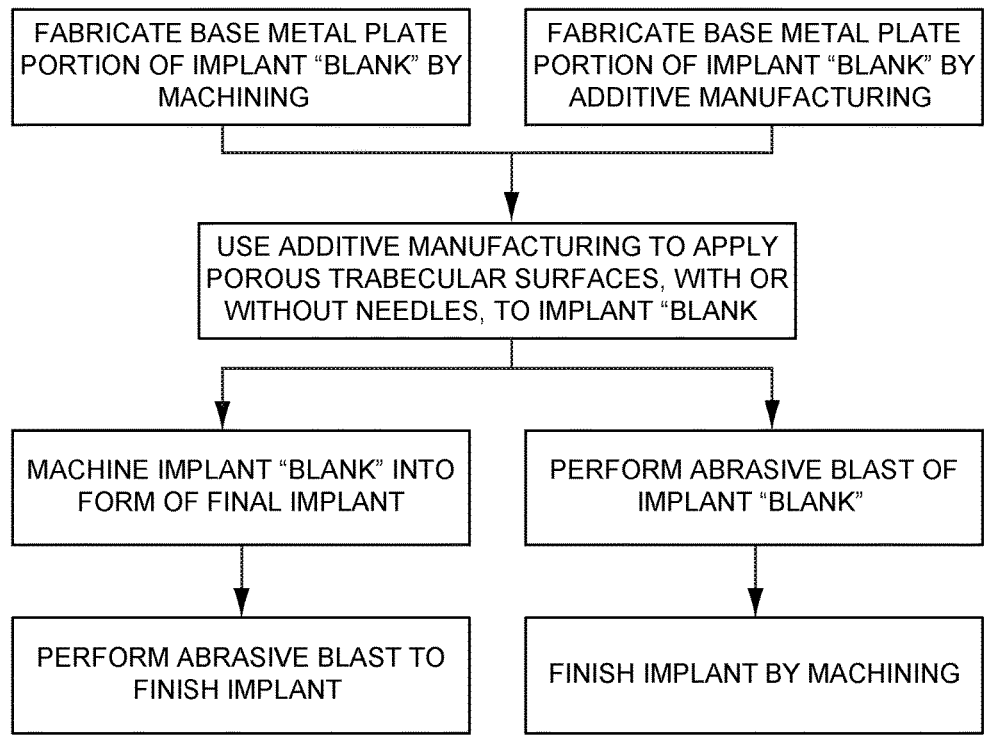

FIG. 7 depicts alternative process flows for manufacturing abrasive-blasted implants in accordance with the invention.

Figure 8A:
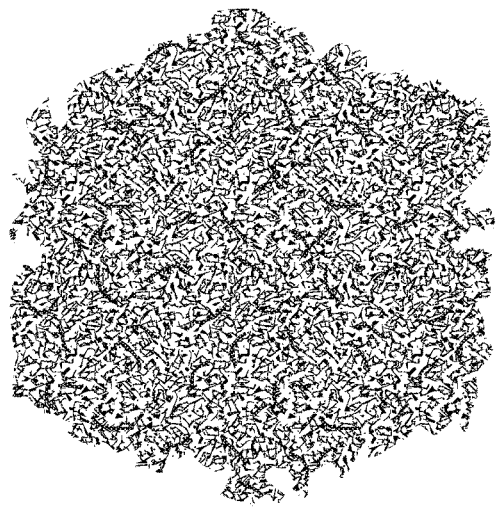

FIG. 8A depicts an illustrative, irregular (e.g., trabecular, osteo-porous, and/or osteo-derived) unit cell appropriate for additive manufacture in accordance with the invention.

Figure 8B:
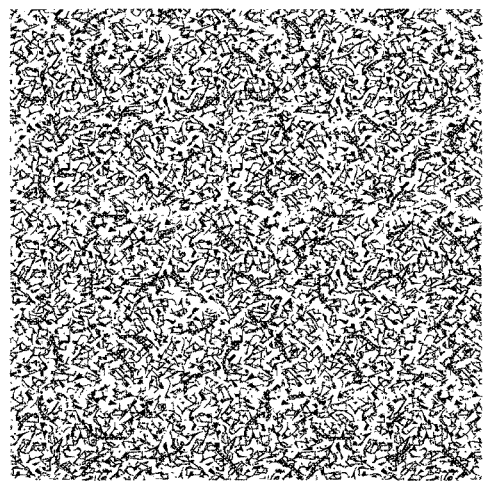

FIG. 8B shows the unit cell of FIG. 8A repeated in a 3×3 array.

Figure 8C:
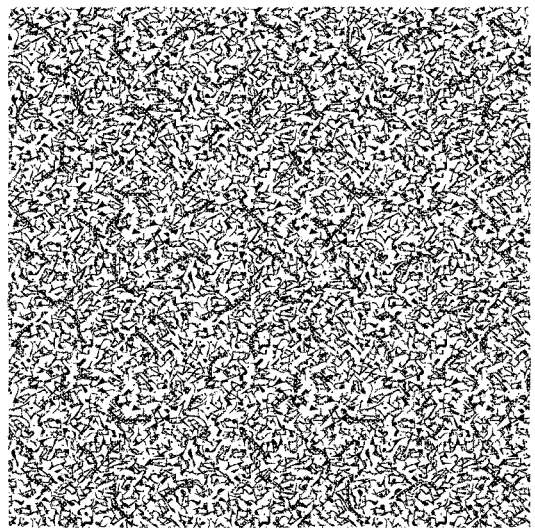

FIG. 8C shows the unit cell of FIG. 8A repeated in a 6×6 array.

Figure 8D:
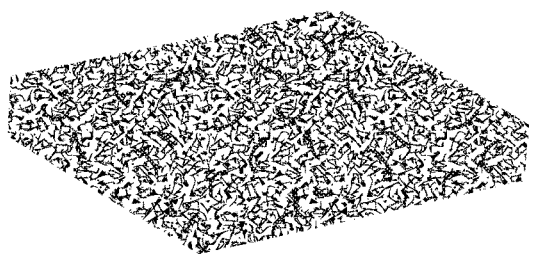

FIG. 8D shows an isometric view of a 9×9 array of the unit cell of FIG. 8A.

Figure 8E:
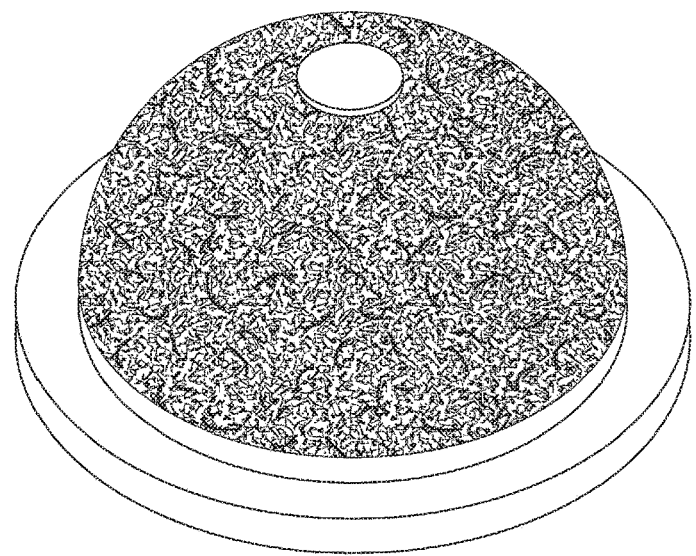

FIG. 8E shows the unit cell of FIG. 8A patterned across the surface of an acetabular shell.

Figure 8F:
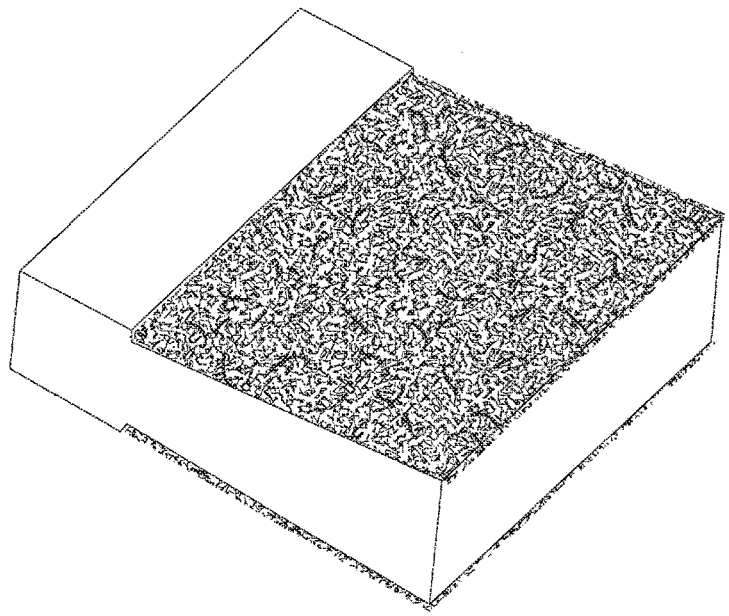

FIGS. 8F shows the unit cell of FIG. 8A patterned across the surface of an ALIF cage "blank".

Figure 9A:
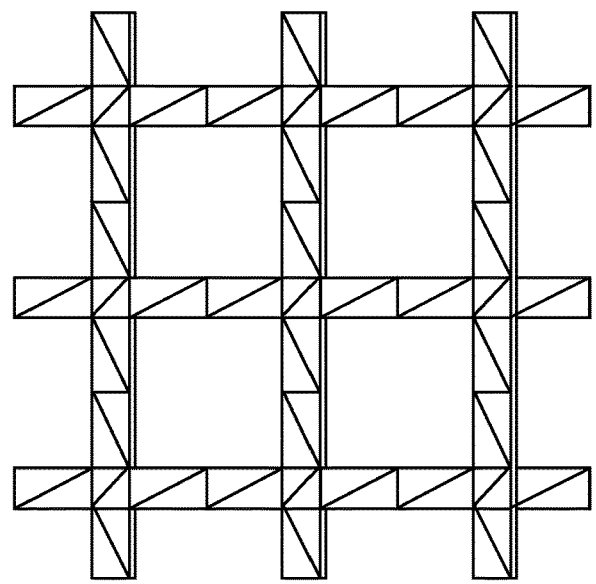

FIG. 9A conceptually depicts a 2-D rendering of a cubic lattice structure, with no node perturbation and no strut size randomization.

Figure 9B:
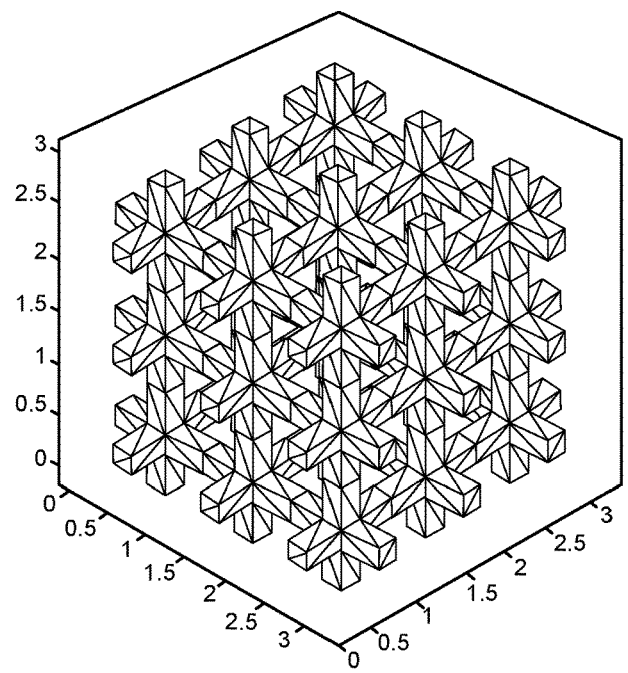

FIG. 9B conceptually depicts a 3-D rendering of the cubic lattice structure, with no node perturbation and no strut size randomization.

Figure 9C:
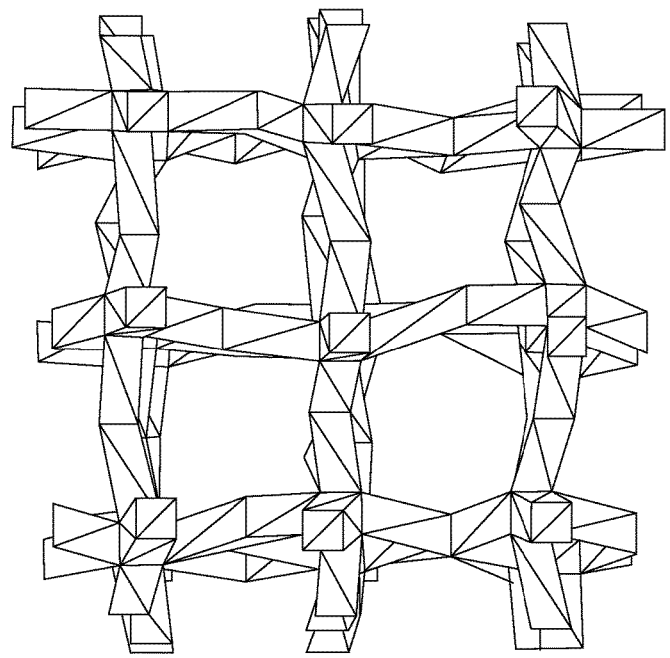

FIG. 9C conceptually depicts a 2-D rendering of a cubic lattice structure, with 20% node perturbation and no strut size randomization.

Figure 9D:
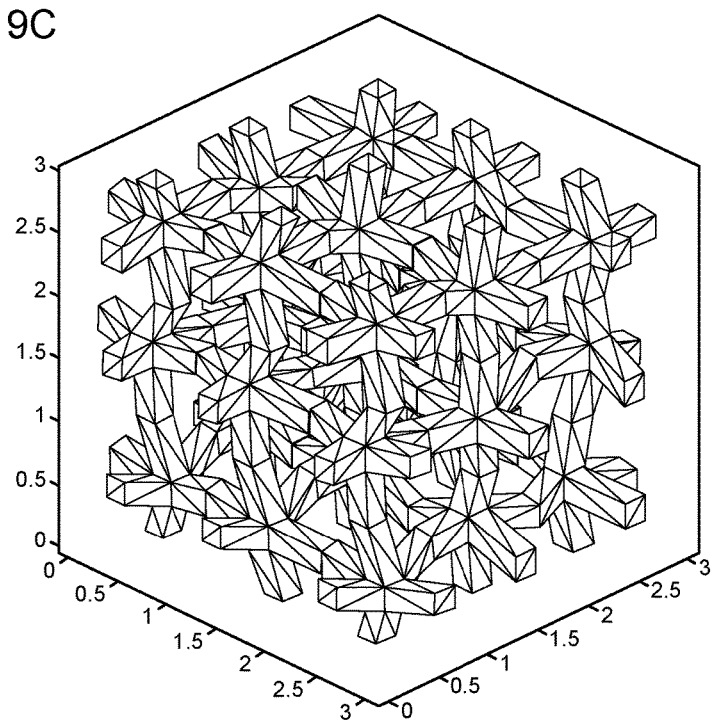

FIG. 9D conceptually depicts a 3-D rendering of the cubic lattice structure, with 20% node perturbation and no strut size randomization.

Figure 9E:
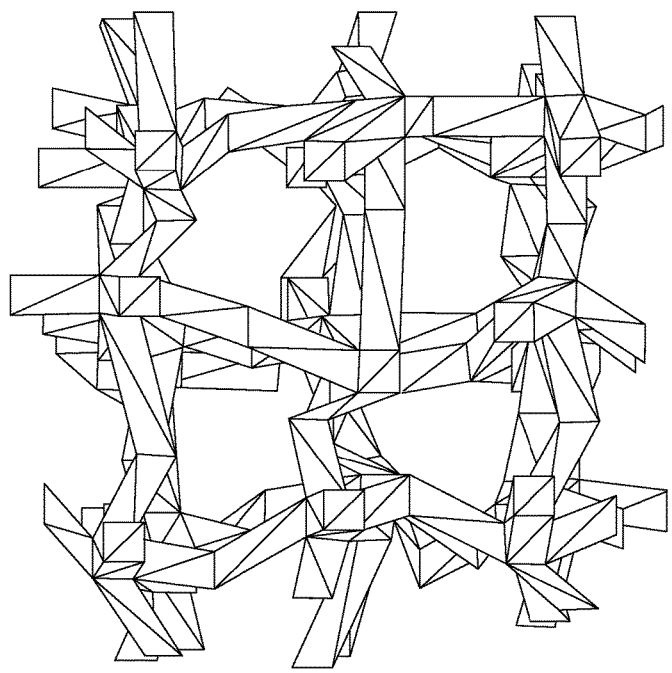

FIG. 9E conceptually depicts a 2-D rendering of a cubic lattice structure, with 40% node perturbation and no strut size randomization.

Figure 9F:
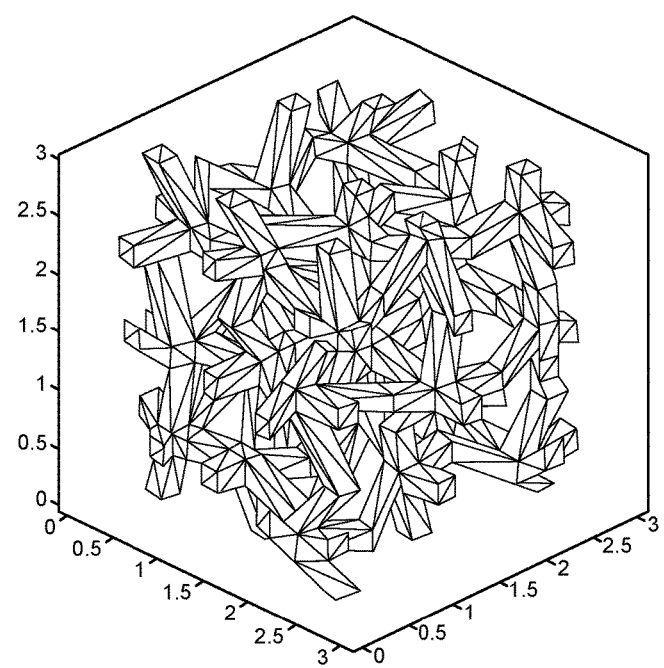

FIG. 9F conceptually depicts a 3-D rendering of the cubic lattice structure, with 40% node perturbation and no strut size randomization.

Figure 9G:
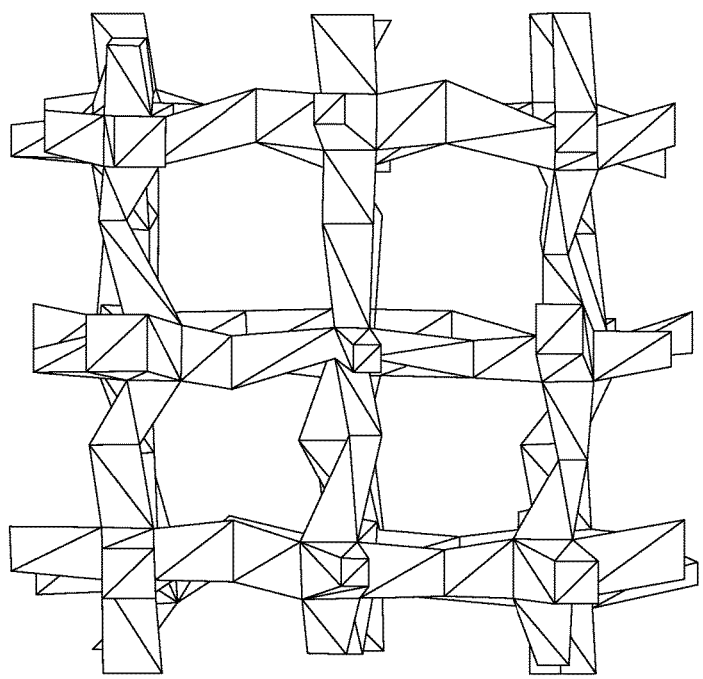

FIG. 9G conceptually depicts a 2-D rendering of a cubic lattice structure, with 20% node perturbation and 100% strut size randomization.

Figure 9H:
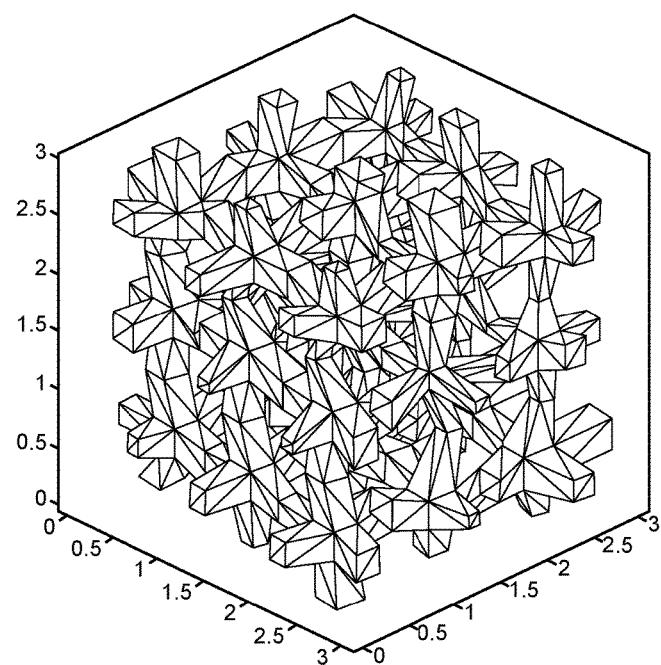

FIG. 9H conceptually depicts a 3-D rendering of the cubic lattice structure, with 20% node perturbation and 100% strut size randomization.

Figure 9I:
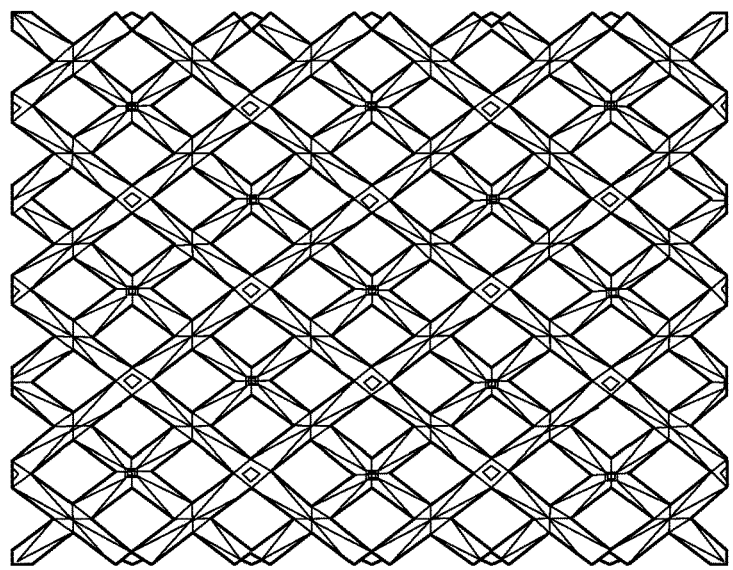

FIG. 9I conceptually depicts a 2-D rendering of a dodecahedron lattice structure, with no node perturbation and no strut size randomization.

Figure 9J:
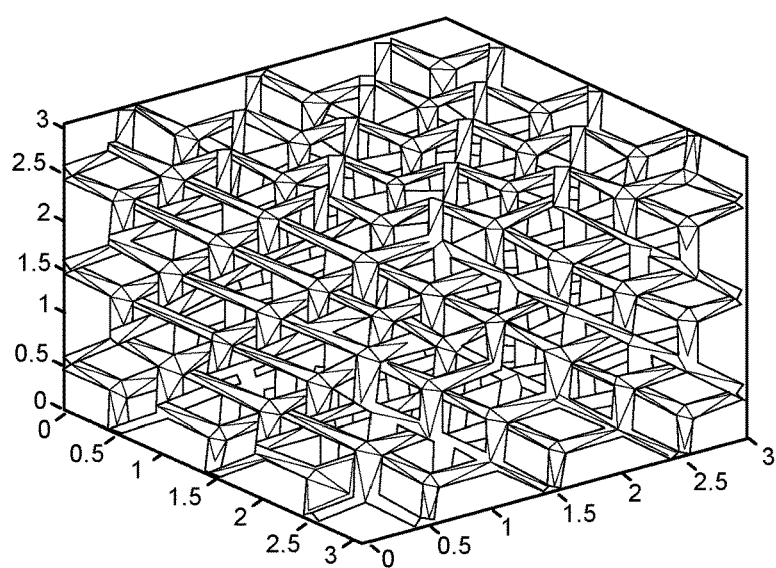

FIG. 9J conceptually depicts a 3-D rendering of the dodecahedron lattice structure, with no node perturbation and no strut size randomization.

Figure 9K:
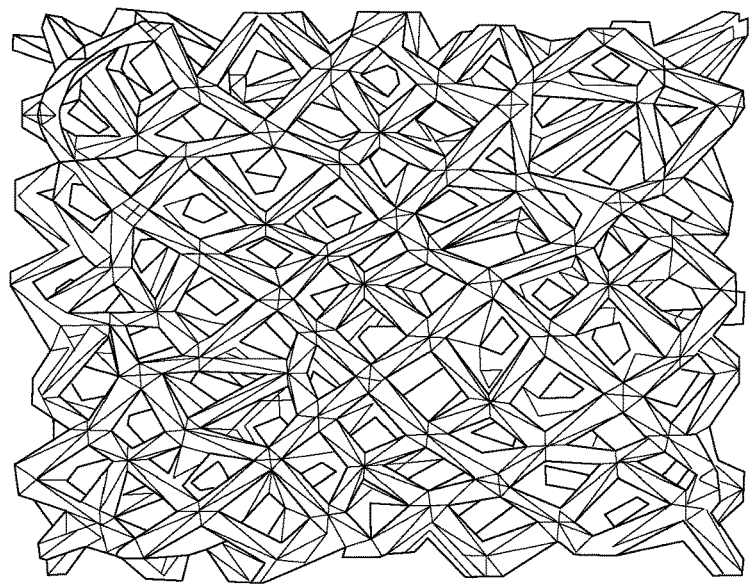

FIG. 9K conceptually depicts a 2-D rendering of a dodecahedron lattice structure, with 20% node perturbation and no strut size randomization.

Figure 9L:
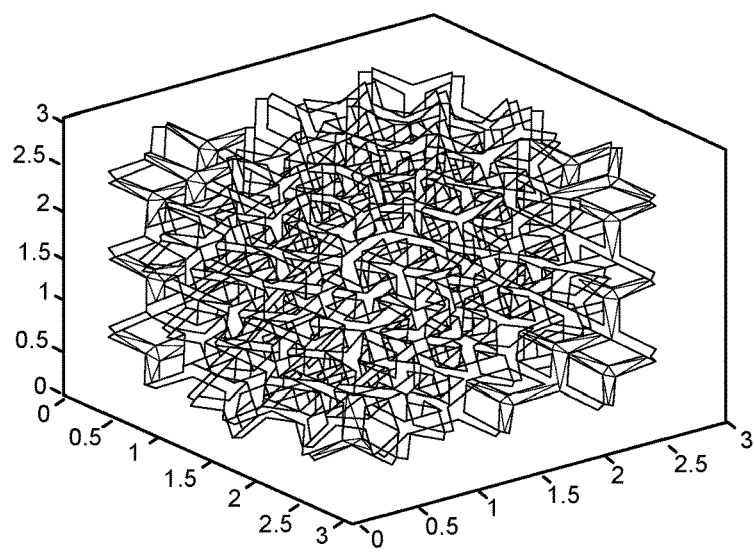

FIG. 9L conceptually depicts a 3-D rendering of the dodecahedron lattice structure, with 20% node perturbation and no strut size randomization.

Figure 10A:
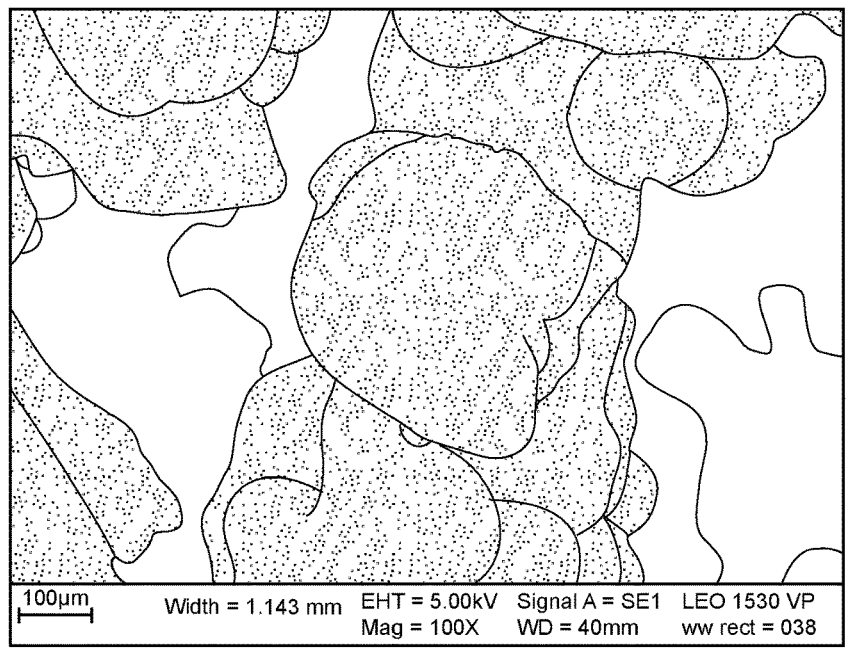
Figure 10B:
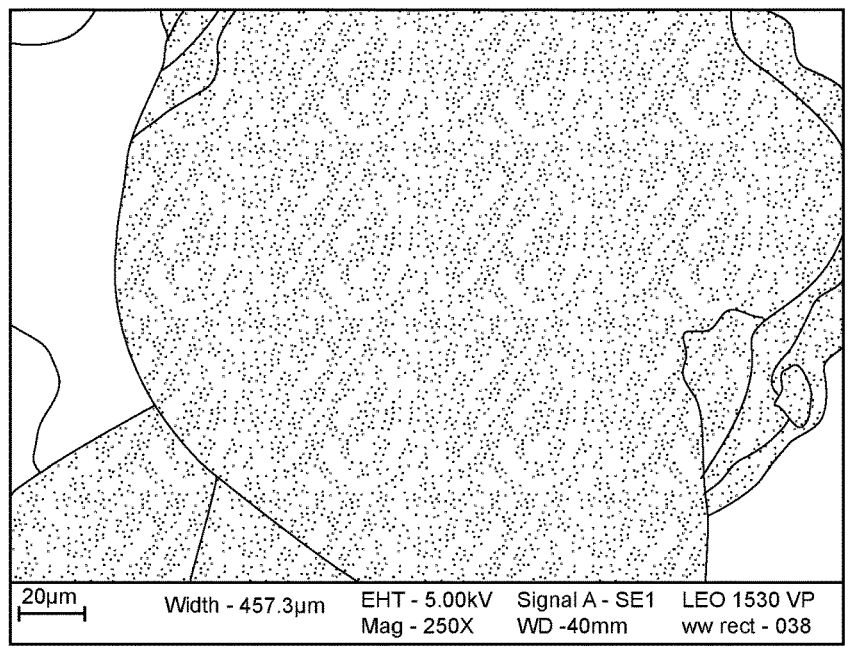

FIGS. 10A and 10B depict exemplary SEM views of porous/trabecular metal sections fabricated by additive manufacturing in accordance with the invention, but not subjected to a post-fabrication abrasive blast step.

Figure 11A:
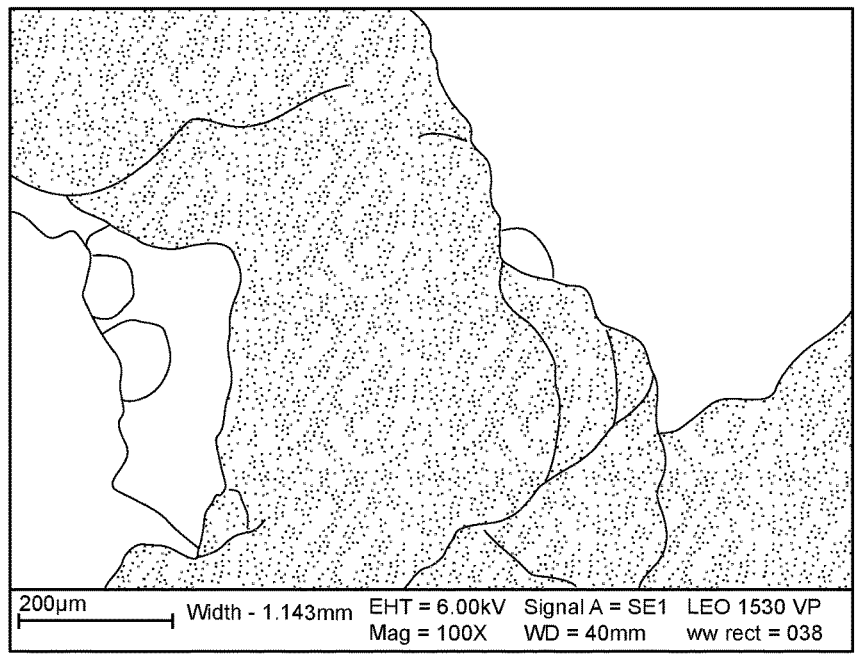
Figure 11B:
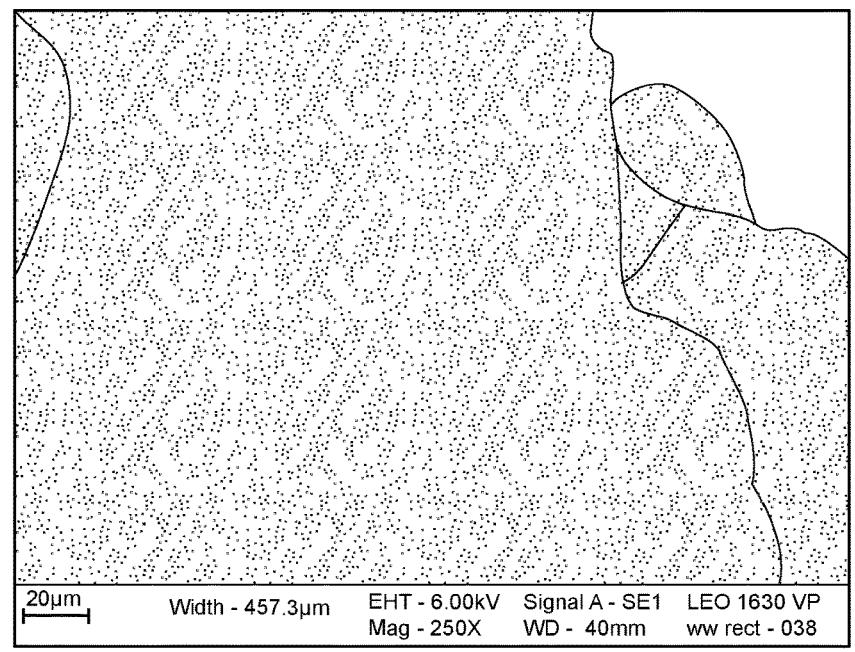

FIGS. 11A and 11B depict exemplary SEM views of porous/trabecular metal sections fabricated by additive manufacturing in accordance with the invention, after being subjected to a post-fabrication abrasive blast step.

Figure 12A:
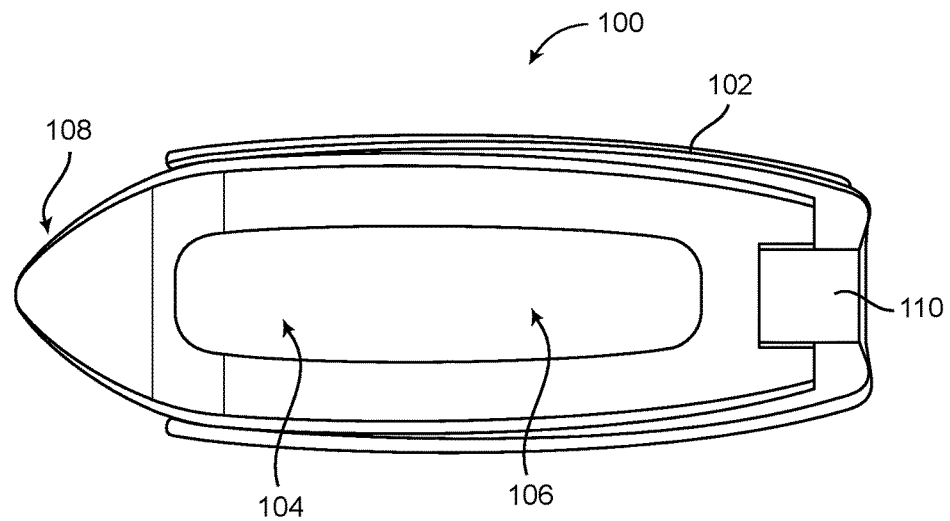
Figure 12B:
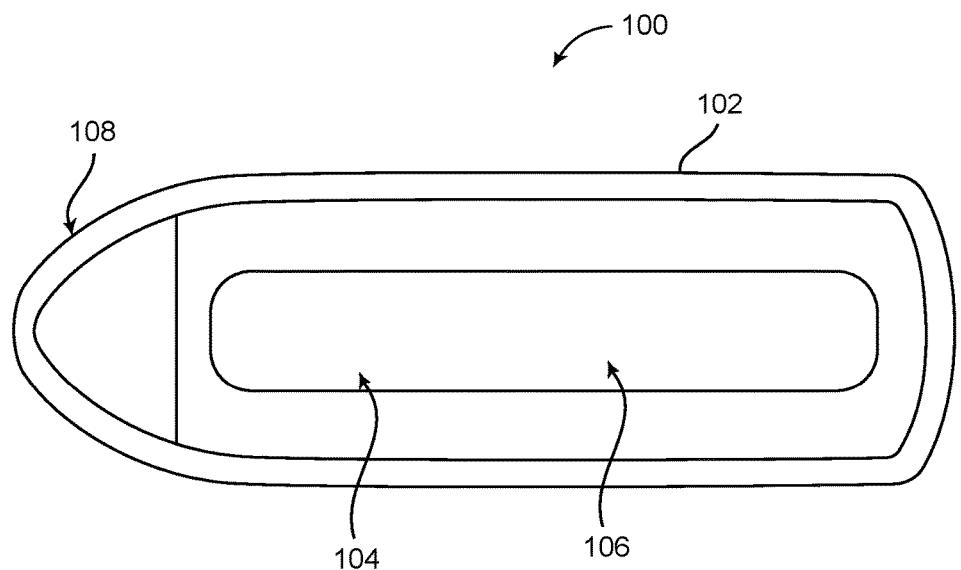

FIGS. 12A and 12B are side and top planar views of one exemplary embodiment of the posterior lumbar interbody fusion (PLIF) cage of the present invention.

Figure 13A:
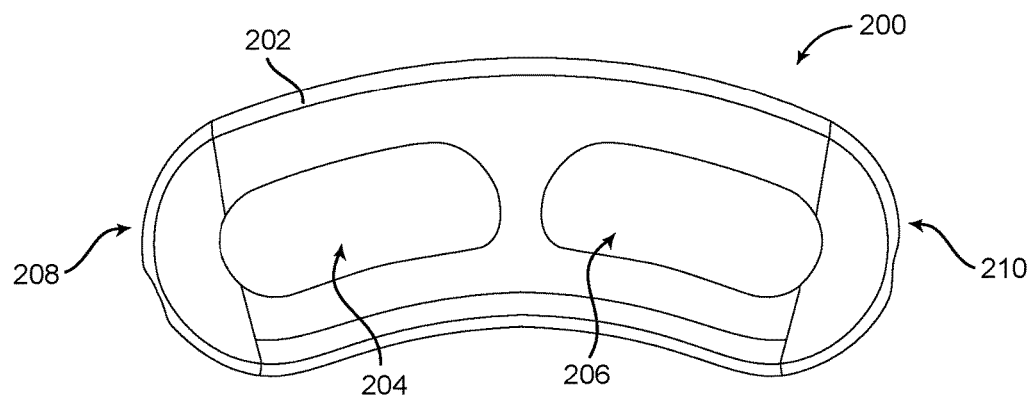
Figure 13B:
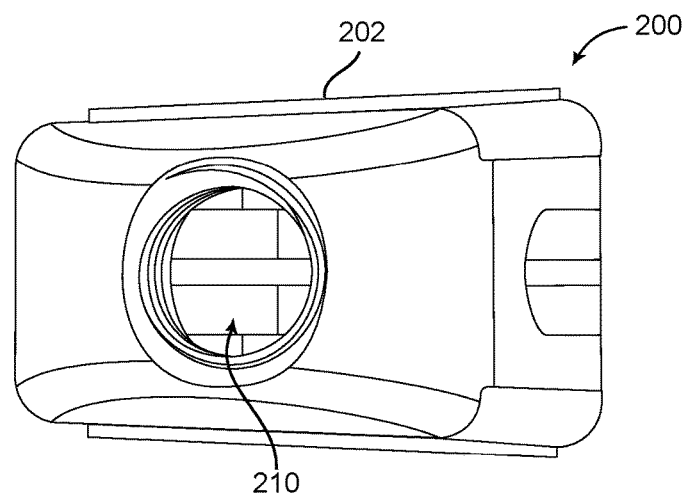
Figure 13C:
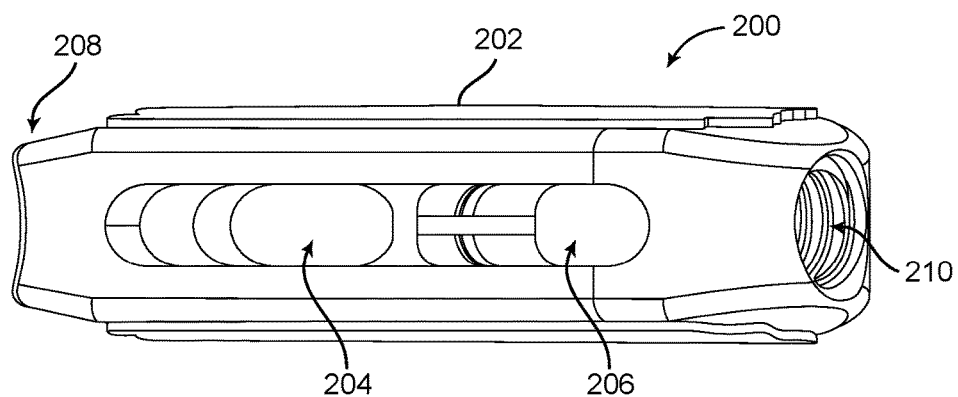

FIGS. 13A-13C are top planar, side planar, and bullet views of one exemplary embodiment of the transforaminal lumbar interbody fusion (TLIF) cage of the present invention.

Figure 14A:
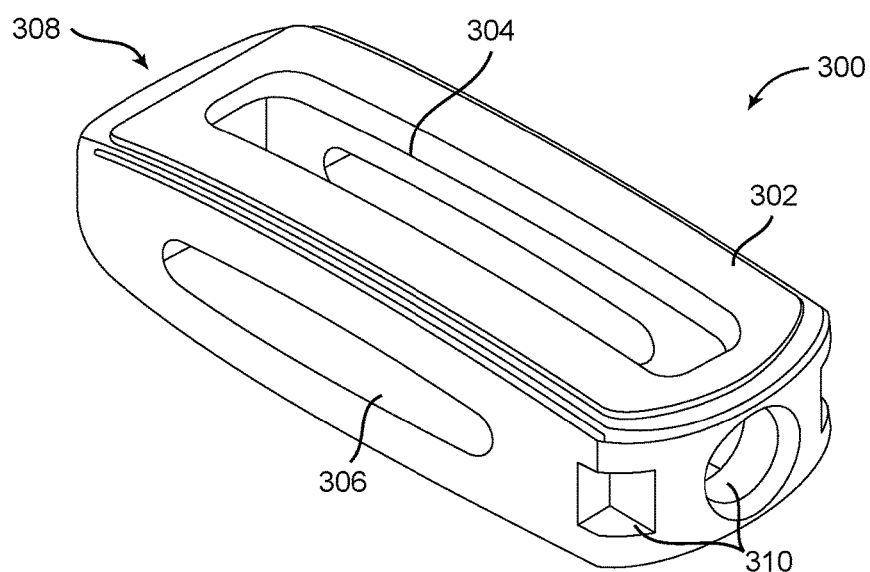
Figure 14B:
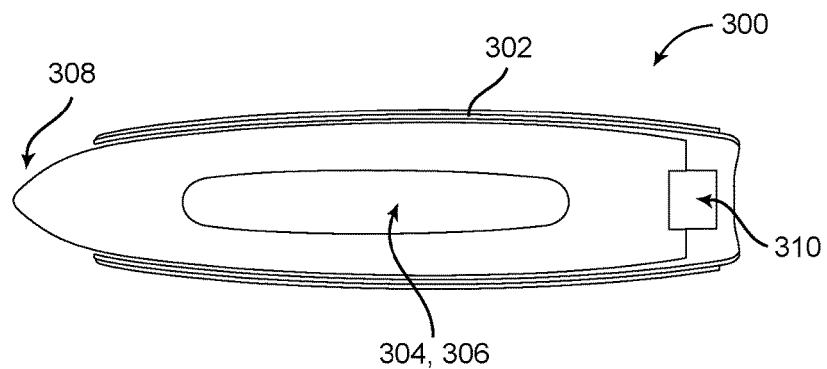
Figure 14C:
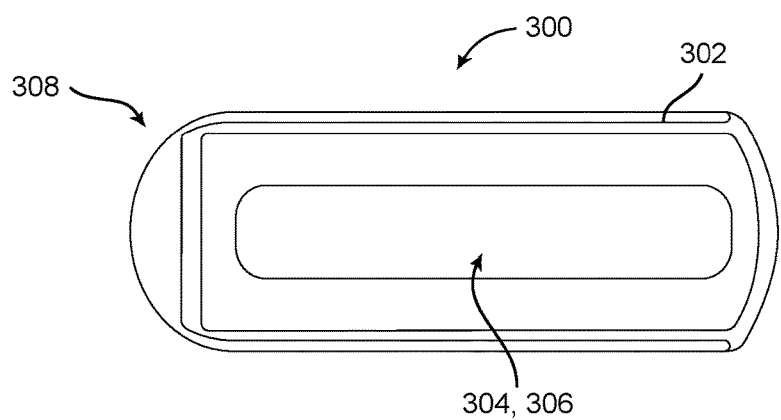

FIG. 14 is perspective, side planar, and top planar views of one exemplary embodiment of the oblique lumbar interbody fusion (OLIF) cage of the present invention.

Figure 15A:
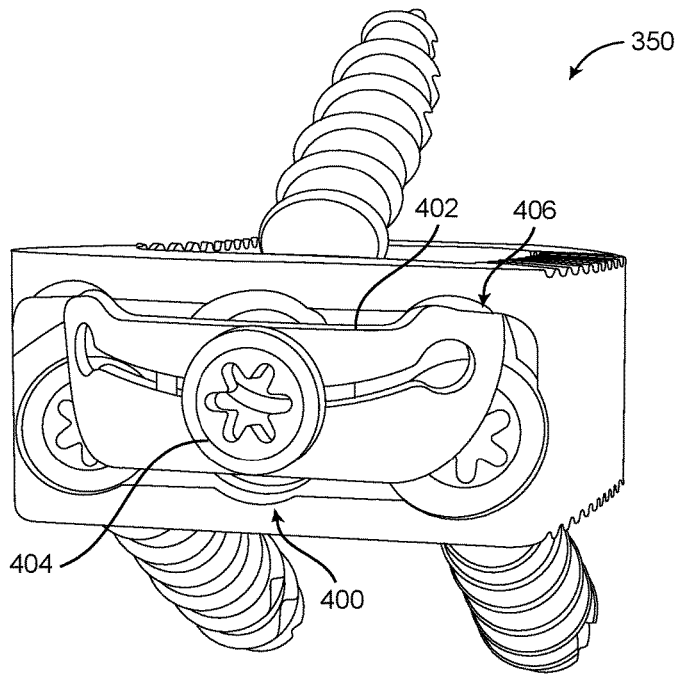
Figure 15B:
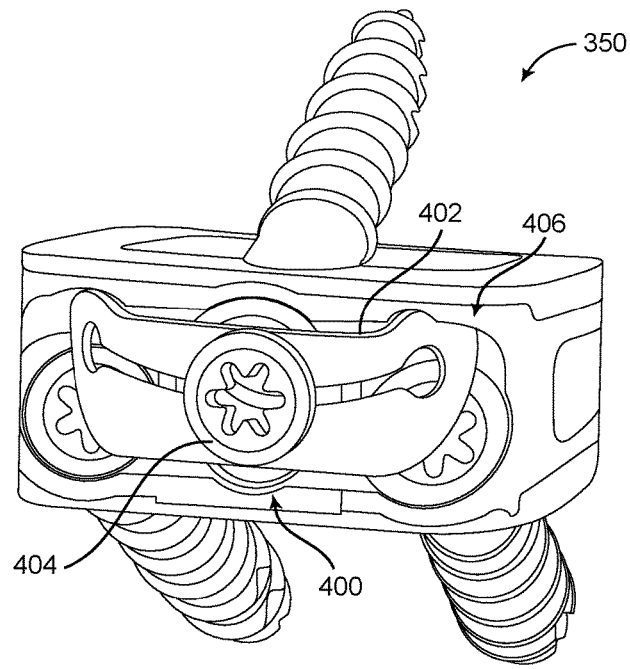

FIG. 15 is perspective views of the cervical cages of the present invention, both in PEEK and titanium embodiments, and incorporating a novel locking mechanism.

Figure 16A:
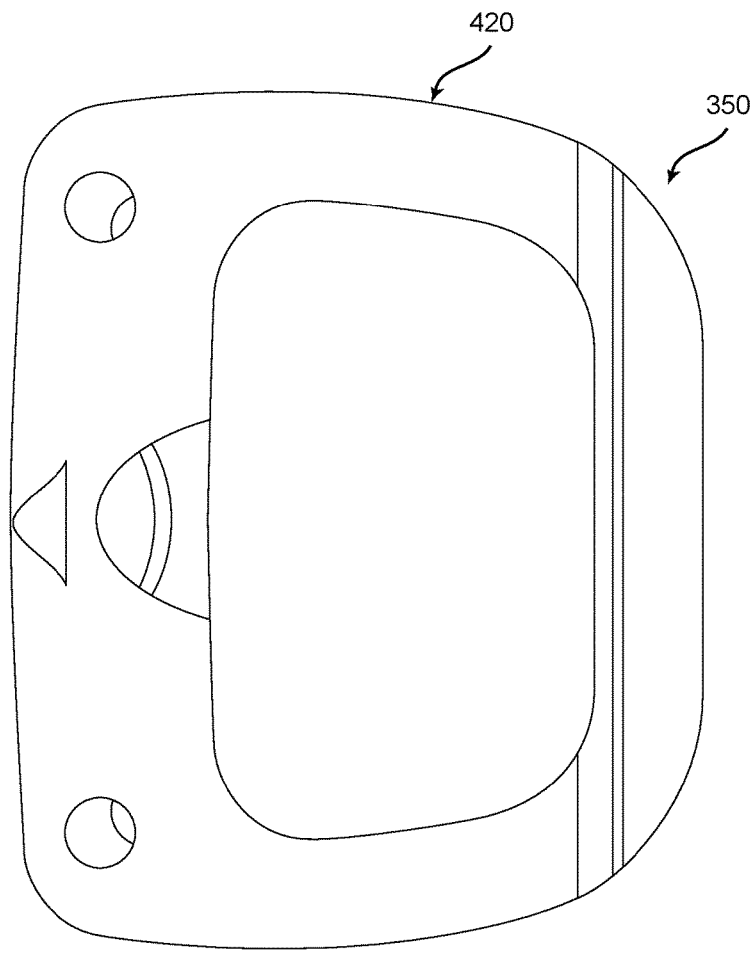
Figure 16B:
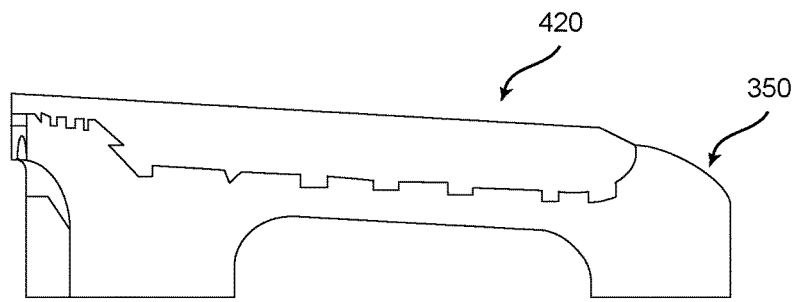
Figure 17B:
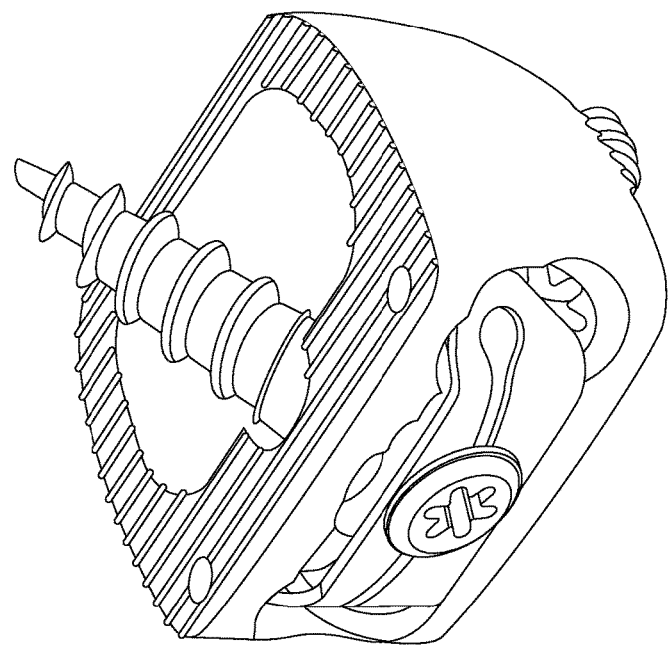
Figure 17A:
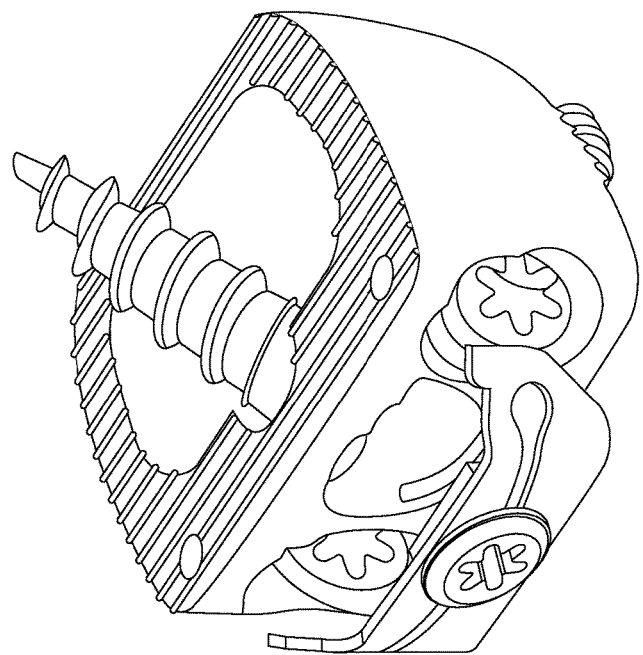
Figure 17D:
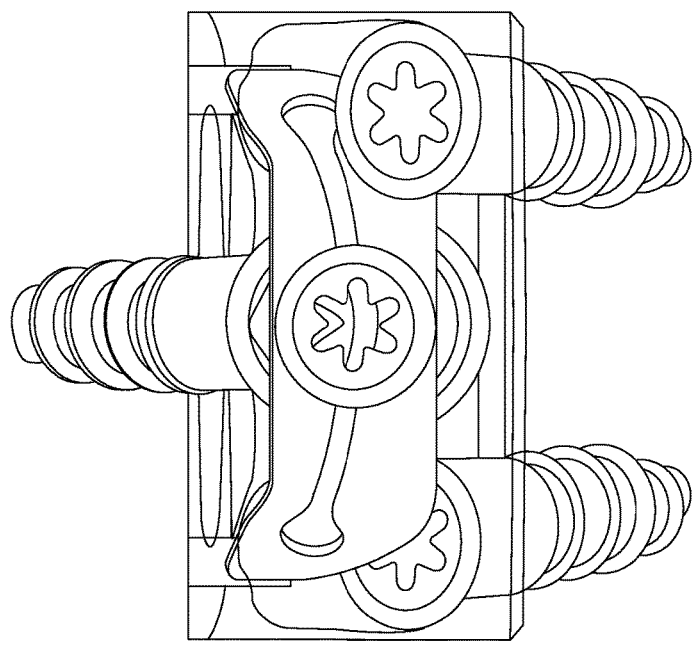
Figure 17C:
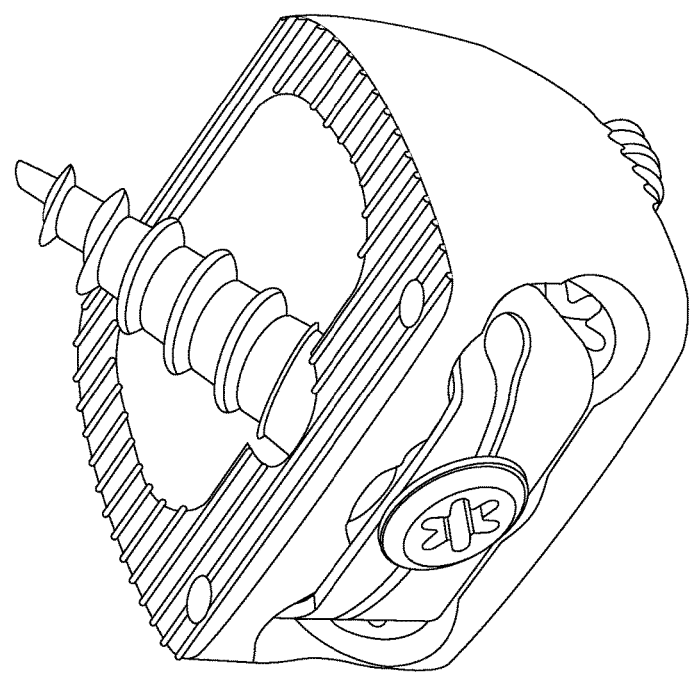

FIG. 16 is top and side planar views of the cervical cage of the present invention, in the titanium embodiment and including at least one porous surface formed by the process of FIG. 1.

FIG. 17 is a series of perspective views illustrating the operation of the locking mechanism of FIG. 15.

Figure 18:
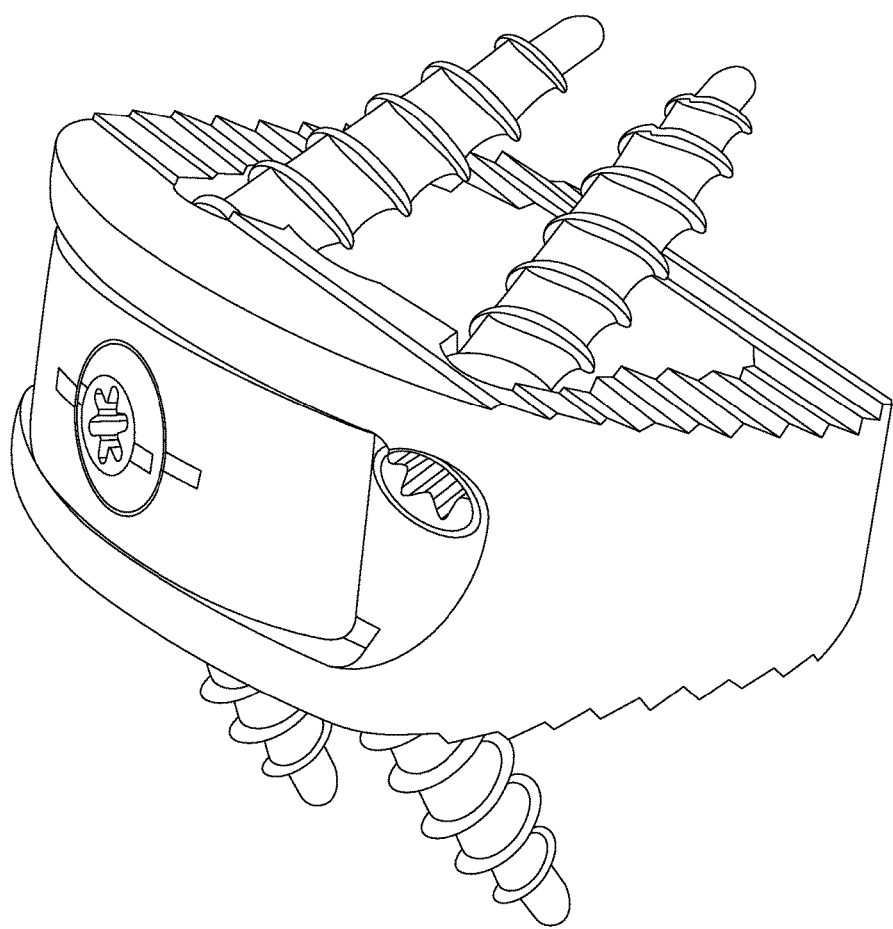

FIG. 18 is a perspective view of the ALIF cage of the present invention, in a PEEK embodiment and including a novel locking mechanism.

Figure 19B:
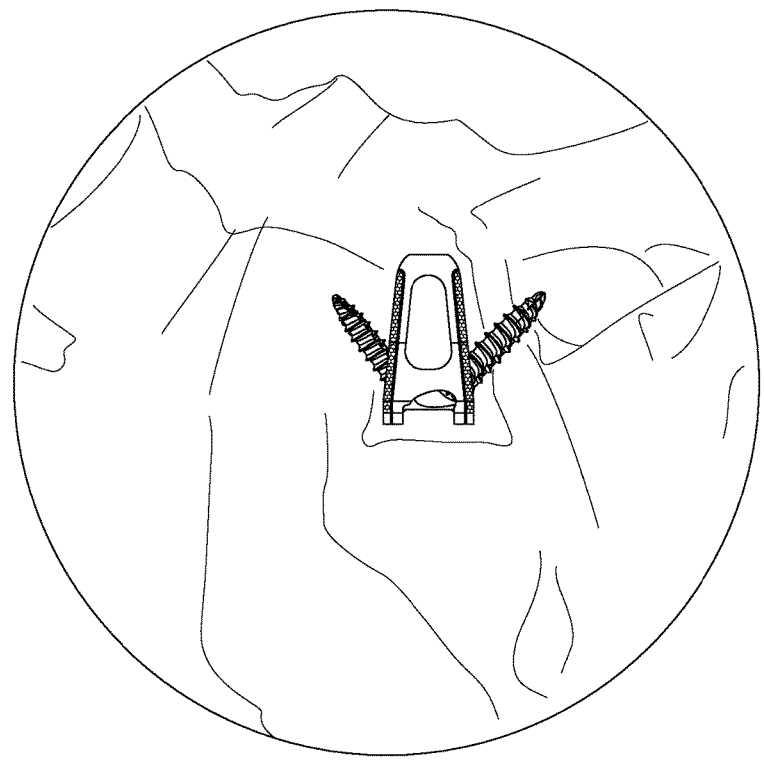
Figure 19A:
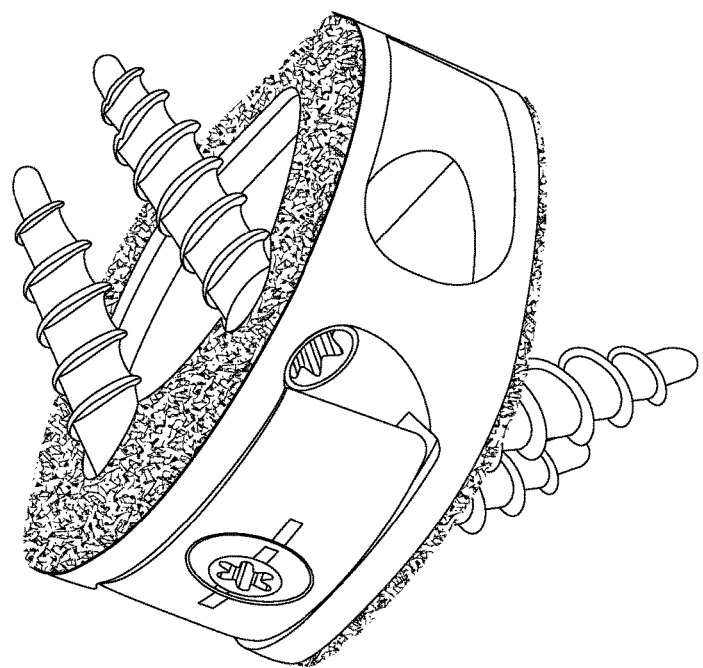

FIG. 19 is a perspective view of the ALIF cage of the present invention, in a PEEK embodiment and including a novel locking mechanism.

Figure 20:
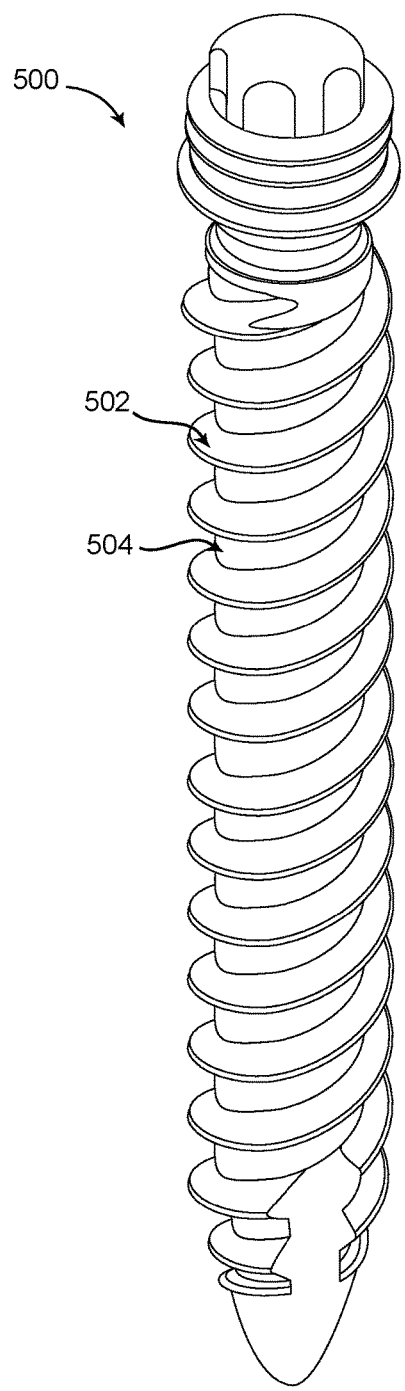

FIG. 20 is a perspective view of the surgical screw of the present invention, incorporating both non-porous and porous regions.

DETAILED DESCRIPTION OF THE INVENTION

Generally speaking, and without intending to be limiting, one aspect of the invention relates to improved medical implants that include, for example, at least the following: a primary structure formed from metal; and at least one needle-populated, metallic surface portion formed on at least one exterior portion of the primary structure, the at least one surface portion located such that it engages with a patient's bone when the implant is implanted in the patient. Such needle-populated, metallic surface portions may contain, for example, a collection of at least fifty, a hundred, two hundred, five-hundred or more needles, and may be further characterized by at least one, two, three, four, five or more of the following characteristicss: (a) the needles in the collection are all oriented substantially normal to the surface portion; (b) the needles in the collection are all oriented in substantially the same direction, with the direction being other than normal to the surface portion; (c) the needles in the collection are all oriented in substantially the same direction, with the direction being other than normal to the surface portion, but within 15 degrees from the normal direction; (d) the needles in the collection are all oriented in substantially the same direction, with the direction being other than normal to the surface portion, and more than 15 degrees from the normal direction; (e) the collection includes needles oriented in at least three different directions relative to the surface portion; (f) the collection includes needles oriented in at least five different directions relative to the surface portion, with all of the needles oriented within 20 degrees from the surface portion normal direction; (g) all of the needles in the collection have substantially the same height; (h) the collection includes needles of at least three different heights; (i) all of the needles in the collection have substantially the same shape; (j) the collection includes needles of at least two different shapes; (k) the needles are distributed substantially uniformly over the surface portion; (l) the needles are distributed non-uniformly over the surface portion; (m) all of the needles in the collection are anchored to the primary structure; (n) most of the needles in the collection are anchored to the primary structure; (o) most of the needles in the collection are anchored to structural elements contained within an osteo-porous, osteo-derived or trabecular coating on the at least one exterior portion of the primary structure; and/or (p) all of the needles in the collection are anchored to structural elements contained within an osteo-porous, osteo-derived or trabecular coating on the at least one exterior portion of the primary structure. The at least one exterior portion preferably includes at least one osteo-porous surface, which may comprise at least one osteo-derived surface. The at least one osteo-porous surface and the needles may be simultaneously formed by an additive manufacturing process, such as, but not limited to, EBM or DMSLS. The primary structure may comprise, for example, a dental implant, a foot-and-ankle or long-bone osteotomy wedge, an intervertebral fusion device, a tibial/femoral augment or spacer, a tibial tray portion of a knee implant, a femoral component portion of a knee implant, a primary hip implant, a revision hip implant, a hip trauma component, an acetabular cup, a hip acetabular augment, or other appropriate structure.

Again, generally speaking, and without intending to be limiting, another aspect of the invention relates to method(s) for making a medical implants with at least one osteo-porous surface by, for example: forming at least a portion of a primary structure of the implant; and forming at least one needle-populated, metallic surface portion on at least one exterior portion of the primary structure using an additive manufacturing technique, the at least one needle-populated surface portion located such that it engages with a patient's bone when the implant is implanted in the patient.

Other aspects of the invention relate to additional features, structures, processes and materials depicted in the figures and/or described herein.

Referring to FIG. 1, the exemplary flow starts with a spongy bone sample, which is micro CT scanned to obtain 3D scan data, which is then processed into solid model data representing an osteo-porous or osteo-derived texture. This texture data is then combined with data representing the overall implant geometry to create a fabrication file for use by either of the manufacturing steps that follow.

The fabrication file may utilize any recognizable solid model specification, such as ".amf" format [see ASTM WK27506—New Specification for Data Exchange Format for Additive Manufacturing], or ".stl" format [see Standard Data Format for Fabbers], and may be embodied on any sort of permanent storage medium (e.g., CD, CD-ROM, flash), semi-permanent (e.g., SRAM) or transitory (e.g., DRAM) storage medium, or embodied in a coded data signal.

Additional background details concerning the fabrication of medical devices using additive techniques can be found in: J. Vehvilainen, "Process and Web Application Development of Medical Applications of Additive Manufacturing," Master's Thesis, Aalto University, School of Science, Dec. 27, 2011 (incorporated by reference).

Referring to FIG. 1A, an additional step can be inserted that adds outwardly-protruding "needles" on the outer surface(s) of the osteo-porous and/or osteo-derived coating(s). Such needles substantially increase the coefficient of friction of the coating. Having a high coefficient of friction is clinically advantageous because it provides stronger initial fixation, which is important before bone is able to grow onto/into the porous structure. Such needles can be uniformly or non-uniformly (as shown in FIG. 1B) distributed along the porous surface. Likewise, various shapes for the needles are possible, including rectangular (as depicted in FIG. 1B), pyramidal, conical, tube-shaped, etc. Also, the needles need not be oriented exactly normal to the exterior surface, but are preferably oriented in a substantially normal (e.g., within +/−15 degrees from normal) orientation. Furthermore, the orientation and/or shape of all needles need not be the same, and the needles may be rendered on selected portions, or the entirety, of the exterior coated surface(s).

Utilizing these or similar techniques, one can efficiently and advantageously form (and/or finish) implants of the sort depicted herein.

Referring to FIG. 6, two preferred process flows for fabricating and finishing implants using an abrasive blast are shown. FIG. 7 shows two alternative flows that employ the blasting technique as well. FIGS. 10A and 10B and 11A and 11B contrastingly depict SEM images of porous implant sections that have and have not undergone an abrasive blasting step. As can be seen from the images, the non-blasted samples are mostly smooth if viewed on the 20 or 100 µm scale, whereas the blasted samples are almost entirely rough, when viewed at similar magnification. This blast process creates a texture approximately 1-20 µm in scale. This is an ideal scale for microtexture because it helps osteoblasts adhere to the titanium struts. The bast material is not deposited on the strut (as an HA coating would be). It simply textures the titanium surface by erosion.

In accordance with the invention, the preferred abrasive blast process utilizes an MCD Apatitic Abrasive (Multi-phased Calcium Phosphate containing HA, TCP and other CaP phases) distributed by Hitemco Medical Applications, Inc., 160 Sweet Hollow Rd., Old Bethpage, N.Y. 11804. The blast media has a 425-180 urn size range. The process utilizes a Comco AccuFlo® standard tank micro-abrasive blaster, equipped with Simoom® Technology and Powder-Gate® valve. Tank orifice is 0.40 inches; Nozzle is 0.060 inches; Pressure is 90+/−5 psi. A satisfactory roughness has been achieved when the blast does not further affect the visual appearance, specifically the color and reflectivity of the device. Machined devices may require a blast touch up.

FIGS. 9A-9L illustratively depict the concept of slightly-irregular lattices that are ideally adapted for additive manu-facturing. As shown in these figures, node perturbation refers to the location of intersecting struts. In accordance with this aspect of the invention, such intersection locations are be randomized such that the node deviates from a uniform lattice by a randomized distance. Strut size ran-domization refers to a deviation in cross-section dimension (e.g., strut diameter). Discrete struts in a lattice could have different cross-sectional sizes, or the struts could have a diameter gradient from one end to the other. These param-eters can be randomized for greater diversity in the lattice's geometry. Such slightly-irregular lattices can be used to fabricate any sort of medical implant for which regular lattices are currently used, including, for example, those disclosed in the incorporated Pressacco et al. and Jones et al. applications.

Another illustrative application of the invention relates to bone fixation/fusion devices of the sort disclosed in U.S. Pat. No. 7,922,765 (incorporated by reference) and/or U.S. Published Applic. No. 2011/0118841 (incorporated by refer-ence) that have been modified to include one or more needle-populated surface(s) in accordance with the teach-ings of the present invention.

Such fusion/fixation devices are preferably fabricated by additive techniques, may utilize multi-circular cross-sec-tional profiles (either uniform or tapered), and preferably include exterior needles, preferably oriented in a direction that would resist removal of the implant. Multi-circular cross-sectional profiles have the distinct advantage of not requiring one or more bore broaching steps, thus making insertion quicker and reducing patient infection risk.

Finally, it should be understood that the novel structures disclosed and enabled by the present invention are not limited exclusively to those manufactured using additive manufacturing. Indeed, as persons skilled in the art will appreciate, other known surface modification techniques—such as, for example, Surfi-Sculpt (U.S. Pat. No. 7,667,158, incorporated by reference herein)—may be used to produce the osteoporous, osteo-derived, and/or needle-containing textures of the inventive implants.

Referring now specifically to FIGS. 2-5, in one exemplary embodiment, the present invention provides an ALIF cage 10 for use in spinal surgical procedures. More specifically, the present invention provides an ALIF cage 10 that includes one or more porous surfaces 12 that promote bony fixation. Preferably, these porous surfaces 12 are formed via an additive manufacturing technique using a titanium alloy powder or the like (as is described in greater detail herein below), thereby providing a unitary structure and eliminat-ing the need to use coatings or bondings for such purpose.

In general, the ALIF cage 10 includes a body structure 14 that defines a hollow interior portion 16 and a plurality of ports 18 through which screws 20 (FIG. 3) or the like are disposed, through the hollow interior portion 16 and into adjacent bone. Optionally, the hollow interior portion 16 is sized and configured to contain bone graft material or the like, to further enhance bony fixation. The screws 20 are shown at a given angle, although any suitable angle(s) for a given application may be utilized, as may any suitable number and size of screws 20.

Advantageously, the ALIF cage 10 consists of a unitary structure that is substantially solid in the middle, for example, and graduates to porous at given surfaces, for example. This provides enhanced structural integrity, allows for the porosity to be carefully controlled in a given area, etc. Alternatively, there may be a relatively sharp dividing line between the solid portion and the porous portions, although it is contemplated that they are integrally formed via the additive manufacturing technique.

The following description is partially taken from U.S. Ser. No. 13/530,048 (which is incorporated in full by reference herein) and explains how the porous surfaces 12 of the ALIF cage 10 are formed.

Generally speaking, and without intending to be limiting, one aspect of the present invention relates to improved medical implants that include, for example, at least the following: a primary structure formed from metal; and at least one needle-populated, metallic surface portion formed on at least one exterior portion of the primary structure, the at least one surface portion located such that it engages with a patient's bone when the implant is implanted in the patient. Such needle-populated, metallic surface portions may con-tain, for example, a collection of at least fifty, a hundred, two hundred, five-hundred or more needles, and may be further characterized by at least one, two, three, four, five or more of the following characteristics: (a) the needles in the collection are all oriented substantially normal to the surface portion; (b) the needles in the collection are all oriented in substantially the same direction, with the direction being other than normal to the surface portion; (c) the needles in the collection are all oriented in substantially the same direction, with the direction being other than normal to the surface portion, but within 15 degrees from the normal direction; (d) the needles in the collection are all oriented in substantially the same direction, with the direction being other than normal to the surface portion, and more than 15 degrees from the normal direction; (e) the collection includes needles oriented in at least three different directions relative to the surface portion; (f) the collection includes needles oriented in at least five different directions relative to the surface portion, with all of the needles oriented within 20 degrees from the surface portion normal direction; (g) all of the needles in the collection have substantially the same height; (h) the collection includes needles of at least three different heights; (i) all of the needles in the collection have substantially the same shape; (j) the collection includes needles of at least two different shapes; (k) the needles are distributed substantially uniformly over the surface portion; (l) the needles are distributed non-uniformly over the surface portion; (m) all of the needles in the collection are anchored to the primary structure; (n) most of the needles in the collection are anchored to the primary structure; (o) most of the needles in the collection are anchored to structural elements contained within an osteo-porous, osteo-derived or trabecular coating on the at least one exterior portion of the primary structure; and/or (p) all of the needles in the collection are anchored to structural elements contained within an osteo-porous, osteo-derived or trabecular coating on the at least one exterior portion of the primary structure. The at least one exterior portion preferably includes at least one osteo-porous surface, which may comprise at least one osteo-derived surface. The at least one osteo-porous surface and the needles may be simultaneously formed by an additive manufacturing process, such as, but not limited to, EBM or DMSLS. The primary structure may comprise, for example, the ALIF cage 10 of the present invention, a dental implant, a foot-and-ankle or long-bone osteotomy wedge, an intervertebral fusion device, a tibial/femoral augment or spacer, a tibial tray portion of a knee implant, a femoral component portion of a knee implant, a primary hip implant, a revision hip implant, a hip trauma component, an acetabular cup, a hip acetabular augment, or other appropriate structure.

Again, generally speaking, and without intending to be limiting, another aspect of the present invention relates to method(s) for making a medical implants with at least one osteo-porous surface by, for example: forming at least a portion of a primary structure of the implant; and forming at least one needle-populated, metallic surface portion on at least one exterior portion of the primary structure using an additive manufacturing technique, the at least one needle-populated surface portion located such that it engages with a patient's bone when the implant is implanted in the patient.

The exemplary flow starts with a spongy bone sample, which is micro CT scanned to obtain 3D scan data, which is then processed into solid model data representing an osteo-porous or osteo-derived texture. This texture data is then combined with data representing the overall implant geometry to create a fabrication file for use by either of the manufacturing steps that follow. The fabrication file may utilize any recognizable solid model specification, such as ".amf" format [see ASTM WK27506—New Specification for Data Exchange Format for Additive Manufacturing], or ".stl" format [see Standard Data Format for Fabbers], and may be embodied on any sort of permanent storage medium (e.g., CD, CD-ROM, flash), semi-permanent (e.g., SRAM) or transitory (e.g., DRAM) storage medium, or embodied in a coded data signal.

Additional background details concerning the fabrication of medical devices using additive techniques can be found in: J. VehvilLinen, "Process and Web Application Development of Medical Applications of Additive Manufacturing," Master's Thesis, Aalto University, School of Science, Dec. 27, 2011 (incorporated by reference.

An additional step can be inserted that adds outwardly-protruding "needles" on the outer surface(s) of the osteo-porous and/or osteo-derived coating(s). Such needles substantially increase the coefficient of friction of the coating. Having a high coefficient of friction is clinically advantageous because it provides stronger initial fixation, which is important before bone is able to grow onto/into the porous structure. Such needles can be uniformly or non-uniformly distributed along the porous surface. Likewise, various shapes for the needles are possible, including rectangular, pyramidal, conical, tube-shaped, etc. Also, the needles need not be oriented exactly normal to the exterior surface, but are preferably oriented in a substantially normal (e.g., within +/−15 degrees from normal) orientation. Furthermore, the orientation and/or shape of all needles need not be the same, and the needles may be rendered on selected portions, or the entirety, of the exterior coated surface(s).

Utilizing these or similar techniques, one can efficiently and advantageously form (and/or finish) implants. Finally, it should be understood that the novel structures disclosed and enabled by the present invention are not limited exclusively to those manufactured using additive manufacturing. Indeed, as persons skilled in the art will appreciate, other known surface modification techniques—such as, for example, Surfi-Sculpt (U.S. Pat. No. 7,667,158, incorporated by reference herein)—may be used to produce the osteoporous, osteo-derived, and/or needle-containing textures of the inventive implants.

FIGS. 12A and 12B are side and top planar views of one exemplary embodiment of the posterior lumbar interbody fusion (PLIF) cage 100 of the present invention. The PLIF cage 100 includes a body structure 102 that defines a substantially hollow interior portion 104 and incorporates one or more windows 106, such that graft material or the like may be disposed within the PLIF cage 100 to promote bony purchase. The PLIF cage 100 also includes a leading edge 108 that is substantially tapered, such that the PLIF cage 100 may be easily disposed in an intervertebral space, and a trailing edge that includes a tool receiving recess 110 or the like. As with all devices of the present invention, the PLIF cage 1001 may be manufactured from PEEK or a metallic material with the porous surface(s) described in detail herein.

FIGS. 13A-13C are top planar, side planar, and bullet views of one exemplary embodiment of the transforaminal lumbar interbody fusion (TLIF) cage 200 of the present invention. The TLIF cage 200 includes a substantially-curved body structure 202 that defines a substantially hollow interior portion 204 and incorporates one or more windows 206, such that graft material or the like may be disposed within the TLIF cage 200 to promote bony purchase. The TLIF cage 200 also includes a leading edge 208 that is substantially tapered, such that the TLIF cage 200 may be easily disposed in an intervertebral space, and a trailing edge that includes a tool receiving recess 210 or the like. As with all devices of the present invention, the TLIF cage 200 may be manufactured from PEEK or a metallic material with the porous surface(s) described in detail herein.

FIG. 14 is perspective, side planar, and top planar views of one exemplary embodiment of the oblique lumbar interbody fusion (OLIF) cage 300 of the present invention. The OLIF cage 300 includes a body structure 302 that defines a substantially hollow interior portion 304 and incorporates one or more windows 306, such that graft material or the like may be disposed within the OLIF cage 300 to promote bony purchase. The OLIF cage 300 also includes a leading edge 308 that is substantially tapered, such that the OLIF cage 300 may be easily disposed in an intervertebral space, and a trailing edge that includes a tool receiving recess 310 or the like. As with all devices of the present invention, the OLIF cage 300 may be manufactured from PEEK or a metallic material with the porous surface(s) described in detail herein.

FIG. 15 is perspective views of the cervical cages 350 of the present invention, both in PEEK and titanium embodiments, and incorporating a novel locking mechanism 400. These cervical cages 350 are similar to the ALIF cage described in detail herein above, further including the novel locking mechanism 400. The novel locking mechanism 400 includes a cover plate 402 that is held in place over one of the primary cage screws using a plate screw 404. When actuated, the plate screw 404 compresses the cover plate 402 against the body structure of the cervical cage 350, driving locking tabs 406 in the corners of the cover plate 402 into corresponding recesses manufactured into the body structure. This locks the primary cage screws into the body structure and prevents them from backing out. Advantageously, at least three points of contact are provided between the cover plate 402 and the body structure to provide the required stability.

FIG. 16 is top and side planar views of the cervical cage of the present invention, in the titanium embodiment and including at least one porous surface 420 formed by the process of FIG. 1. In this exemplary embodiment, the porous surface 420 does not cover the insertion edge and is thinner at the anterior edge to allow support material for the cover plate 402 and plate screw 404.

FIG. 17 is a series of perspective views illustrating the operation of the locking mechanism of FIG. 15.

FIG. 18 is a perspective view of the ALIF cage of the present invention, in a PEEK embodiment and including a novel locking mechanism. FIG. 19 is a perspective view of the ALIF cage of the present invention, in a PEEK embodiment and including a novel locking mechanism. These ALIF cages operates in a manner similar to the cervical cages described herein above.

FIG. 20 is a perspective view of the surgical screw 500 of the present invention, incorporating both porous regions 502 and non-porous regions 504. Specifically, in this exemplary embodiment, the porous regions are disposed at the threads to promote bony purchase.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A surgical implant device, comprising:
    a metallic body portion defining a plurality of ports, the body portion comprising one or more metallic osteo-porous surfaces osteo-derived from one or more spongy bone surfaces to approximate the texture of the one or more spongy bone surfaces and comprising a plurality of metallic protruding structures disposed one or more of on and through the one or more osteo-porous surfaces, wherein the body portion and the one or more osteo-porous surfaces comprising the plurality of protruding structures disposed one or more of on and through the one or more osteo-porous surfaces are integrally formed, wherein one or more osteo-porous surfaces and the plurality of protruding structures disposed one or more of on and through the one or more osteo-porous surfaces are both configured to promote bony ingrowth;
    wherein an exterior surface of each of the plurality of protruding structures is roughened to further promote bony ingrowth;
    a plurality of bone screws disposed partially through the plurality of ports defined by the body portion;
    a locking plate disposed over a head portion of at least one of the plurality of bone screws and engaging a plurality of recesses manufactured into a side of the body portion; and
    a screw operable for compressing the locking plate against the side of the body portion.

2. The surgical implant device of claim 1, wherein the one or more surfaces comprising the plurality of protruding structures are formed by an additive manufacturing process.

3. The surgical implant device of claim 1, wherein the plurality of protruding structures comprise a plurality of needles.

4. The surgical implant device of claim 1, wherein the plurality of protruding structures comprise a plurality of needles that are disposed perpendicular to the body portion.

5. The surgical implant device of claim 1, wherein the plurality of protruding structures comprise a plurality of needles that are disposed at an angle to the body portion.

6. The surgical implant device of claim 1, wherein the plurality of protruding structures comprise a plurality of needles that comprise titanium.

7. The surgical implant device of claim 1, wherein the body portion defines a hollow interior cavity.

8. The surgical implant device of claim 1, wherein the body portion defines one or more ports that are configured to allow bony ingrowth.

9. The surgical implant device of claim 1, wherein the surgical implant device comprises an anterior lumbar interbody fusion cage or a cervical cage.

* * * * *